US011951111B2

(12) United States Patent
Chiarella et al.

(10) Patent No.: US 11,951,111 B2
(45) Date of Patent: *Apr. 9, 2024

(54) IMMEDIATE RELEASE MULTILAYER TABLET

(71) Applicant: Alkermes Pharma Ireland Limited, Dublin (IE)

(72) Inventors: Renato A. Chiarella, Dublin (IE); Hector Guzman, Dublin (IE); Paul Hurley, Dublin (IE); David Manser, Dublin (IE); Kristopher Perkin, Dublin (IE)

(73) Assignee: Alkermes Pharma Ireland Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/327,229

(22) Filed: Jun. 1, 2023

(65) Prior Publication Data
US 2023/0310451 A1 Oct. 5, 2023

Related U.S. Application Data

(63) Continuation of application No. 17/855,242, filed on Jun. 30, 2022, now Pat. No. 11,707,466, which is a continuation of application No. PCT/EP2021/081585, filed on Nov. 12, 2021.

(60) Provisional application No. 63/113,067, filed on Nov. 12, 2020.

(51) Int. Cl.
*A61K 9/28* (2006.01)
*A61K 9/20* (2006.01)
*A61K 9/24* (2006.01)
*A61K 31/485* (2006.01)
*A61K 31/5513* (2006.01)

(52) U.S. Cl.
CPC ........ *A61K 31/5513* (2013.01); *A61K 9/2013* (2013.01); *A61K 9/2018* (2013.01); *A61K 9/2027* (2013.01); *A61K 9/2054* (2013.01); *A61K 9/209* (2013.01); *A61K 9/2095* (2013.01); *A61K 31/485* (2013.01)

(58) Field of Classification Search
None
See application file for complete search history.

(56) References Cited

U.S. PATENT DOCUMENTS

| | | |
|---|---|---|
| 3,332,950 A | 7/1967 | Blumberg et al. |
| 3,856,795 A | 12/1974 | Yardley |
| 3,957,793 A | 5/1976 | Wentland et al. |
| 4,032,529 A | 6/1977 | Wentland et al. |
| 4,100,288 A | 7/1978 | Merz et al. |
| RE29,943 E | 3/1979 | Wentland et al. |
| 4,161,597 A | 7/1979 | Olofson et al. |
| 4,176,186 A | 11/1979 | Goldberg et al. |
| 4,205,171 A | 5/1980 | Albertson |
| 4,373,139 A | 2/1983 | Beesley |
| 4,374,139 A | 2/1983 | Mohacsi |
| 4,451,470 A | 5/1984 | Ganti |
| 4,464,378 A | 8/1984 | Hussain |
| 4,473,573 A | 9/1984 | Merz et al. |
| 4,489,079 A | 12/1984 | Giudice et al. |
| 4,649,200 A | 3/1987 | Portoghese et al. |
| 4,929,622 A | 5/1990 | Allen et al. |
| 5,258,386 A | 11/1993 | Newman et al. |
| 5,607,941 A | 3/1997 | Merz et al. |
| 5,847,142 A | 12/1998 | Mudryk et al. |
| 6,365,594 B1 | 4/2002 | Dondio et al. |
| 6,784,187 B2 | 8/2004 | Wentland |
| 6,812,236 B2 | 11/2004 | Gibson et al. |
| 6,887,998 B2 | 5/2005 | Wentland |
| 7,057,035 B2 | 6/2006 | Wentland et al. |
| 7,244,866 B2 | 7/2007 | Carson et al. |
| 7,262,298 B2 | 8/2007 | Wentland |
| 7,265,226 B2 | 9/2007 | Wentland |
| 7,557,119 B2 | 7/2009 | Wentland |
| 7,956,187 B2 | 6/2011 | Wentland |
| 8,026,252 B2 | 9/2011 | Wentland |
| 8,138,169 B2 | 3/2012 | Oronsky et al. |
| 8,252,929 B2 | 8/2012 | Wentland |
| 8,263,807 B2 | 9/2012 | Wentland |
| 8,354,534 B2 | 1/2013 | Arnelle et al. |
| 8,436,175 B2 | 5/2013 | Wentland |
| 8,642,615 B2 | 2/2014 | Wentland |
| 8,680,112 B2 | 3/2014 | Wentland |

(Continued)

FOREIGN PATENT DOCUMENTS

| | | |
|---|---|---|
| BE | 634402 A | 1/1964 |
| CA | 2587074 A1 | 5/2006 |

(Continued)

OTHER PUBLICATIONS

Sun et al., "Combination of olanzapine and samidorphan has no clinically relevant effects on ECG parameters, including the QTc interval: Results from a phase 1 QT/QTc study." Progress in Neuropsychopharmacology & Biological Psychiatry 100, pp. 1-9. (Year: 2020).*
"Link Between Fast Food and Depression Confirmed", ScienceDaily, Plataforma SINC, Mar. 30, 2012.
Akhtar Muneeba et al: "Bilayer tablets: A developing novel drug delivery system", Journal of Drug Delivery Science and Technology, vol. 60, Sep. 11, 2020 (Sep. 11, 2020), p. 102079, XP055909728, FR ISSN: 1773-2247, DOI: 10.1016/j.jddst.2020.102079.
Alkermes: "Alkermes Initiates Clinical Study of ALKS 5461 for Treatment-Resistant Depression," Retrieved from the internet: URL: http://www.pipelinereview.com/index.php/2011061543028/Neurology-and-Psychiatry/Alkermes-Initiates-Clinical-Study-of-ALKS-5461-for-Treatment-Resistant-Depression.html, retrieved on Mar. 14, 2013 (Jul. 2011).

(Continued)

Primary Examiner — Susan T Tran
(74) Attorney, Agent, or Firm — Goodwin Procter LLP

(57) ABSTRACT

Described herein, in part, are tablets, such as immediate release multi-layer or bilayer tablets for orally delivering olanzapine and samidorphan, methods of using said tablets in the treatment of disorders described herein, and kits comprising said tablets.

13 Claims, 25 Drawing Sheets

(56) References Cited

U.S. PATENT DOCUMENTS

| | | |
|---|---|---|
| 8,778,960 B2 | 7/2014 | Deaver et al. |
| 8,802,655 B2 | 8/2014 | Wentland |
| 8,822,488 B2 | 9/2014 | Deaver et al. |
| 9,119,848 B2 | 9/2015 | Silverman et al. |
| 9,126,977 B2 | 9/2015 | Deaver et al. |
| 9,133,125 B2 | 9/2015 | Blumberg et al. |
| 9,211,293 B2 | 12/2015 | Deaver et al. |
| 9,416,137 B2 | 8/2016 | Blumberg et al. |
| 9,517,235 B2 | 12/2016 | Deaver et al. |
| 9,656,961 B2 | 5/2017 | Blumberg et al. |
| 9,682,936 B2 | 6/2017 | Blumberg et al. |
| 9,917,235 B2 | 3/2018 | Kim |
| 9,943,514 B2 | 4/2018 | Deaver et al. |
| 10,112,903 B2 | 10/2018 | Remenar et al. |
| 10,231,963 B2 | 3/2019 | Blumberg et al. |
| 10,287,250 B2 | 5/2019 | Blumberg et al. |
| 10,300,054 B2 | 5/2019 | Deaver et al. |
| 10,716,785 B2 | 7/2020 | Deaver et al. |
| 10,736,890 B2 | 8/2020 | Blumberg et al. |
| 10,752,592 B2 | 8/2020 | Blumberg et al. |
| 10,822,306 B2 | 11/2020 | Remenar et al. |
| 11,185,541 B2 | 11/2021 | Deaver et al. |
| 11,241,425 B2 | 2/2022 | Deaver et al. |
| 11,351,166 B2 | 6/2022 | Deaver et al. |
| 2002/0099216 A1 | 7/2002 | Gibson et al. |
| 2003/0181475 A1 | 9/2003 | Kaiko et al. |
| 2003/0187009 A1 | 10/2003 | Wentland |
| 2004/0187009 A1 | 9/2004 | Ebata |
| 2004/0192715 A1 | 9/2004 | Chasin et al. |
| 2004/0254208 A1 | 12/2004 | Weber et al. |
| 2005/0176645 A1 | 8/2005 | Mickle et al. |
| 2005/0182258 A1 | 8/2005 | Schmidhammer et al. |
| 2005/0215799 A1 | 9/2005 | Wentland et al. |
| 2006/0030580 A1 | 2/2006 | Wentland |
| 2006/0063792 A1 | 3/2006 | Dolle et al. |
| 2007/0021457 A1 | 1/2007 | Wentland |
| 2007/0099947 A1 | 5/2007 | Dean et al. |
| 2007/0238748 A1 | 10/2007 | Wentland |
| 2008/0004260 A1 | 1/2008 | Singh |
| 2008/0004324 A1 | 1/2008 | Barak |
| 2008/0234306 A1 | 9/2008 | Perez et al. |
| 2008/0317843 A1* | 12/2008 | Jenkins .......... A61P 11/00 424/464 |
| 2009/0053329 A1 | 2/2009 | Peters et al. |
| 2009/0197905 A1 | 8/2009 | Wentland |
| 2009/0209569 A1 | 8/2009 | Arnelle et al. |
| 2009/0247562 A1 | 10/2009 | Wentland |
| 2009/0311347 A1 | 12/2009 | Oronsky et al. |
| 2010/0035910 A1 | 2/2010 | Wang et al. |
| 2010/0048906 A1 | 2/2010 | Wang et al. |
| 2010/0130512 A1 | 5/2010 | Wentland |
| 2010/0190817 A1 | 7/2010 | Wentland |
| 2010/0240691 A1 | 9/2010 | Turncliff et al. |
| 2011/0136848 A1 | 6/2011 | Silverman |
| 2012/0010412 A1 | 1/2012 | Duncan |
| 2013/0231361 A1 | 9/2013 | Wentland |
| 2013/0281388 A1 | 10/2013 | Deaver et al. |
| 2014/0303371 A1 | 10/2014 | Duncan |
| 2015/0011768 A1 | 1/2015 | Wentland |
| 2016/0051538 A1 | 2/2016 | Deaver et al. |
| 2021/0015812 A1 | 1/2021 | Deaver et al. |
| 2021/0038594 A1 | 2/2021 | Deaver et al. |
| 2023/0301922 A1* | 9/2023 | McKinney .......... A61P 25/24 424/472 |

FOREIGN PATENT DOCUMENTS

| | | |
|---|---|---|
| DE | 2254298 A1 | 5/1974 |
| EP | 0254120 A2 | 1/1988 |
| EP | 0632041 A1 | 1/1995 |
| EP | 1359146 A2 | 11/2003 |
| ES | 2121553 A1 | 11/1998 |
| GB | 874217 A | 8/1961 |
| GB | 981046 A | 1/1965 |
| GB | 1340720 A | 12/1973 |
| JP | 40010154 B4 | 5/1965 |
| JP | 5231100 B2 | 7/2013 |
| WO | WO-1993/011761 A1 | 6/1993 |
| WO | WO-1997/025331 A1 | 7/1997 |
| WO | WO-1998/052929 A1 | 11/1998 |
| WO | WO-2001/012197 A1 | 2/2001 |
| WO | WO-2001/037785 A2 | 5/2001 |
| WO | WO-2002/036573 A2 | 5/2002 |
| WO | WO-2003/101963 A1 | 12/2003 |
| WO | WO-2004/005924 A1 | 1/2004 |
| WO | WO-2004/007449 A1 | 1/2004 |
| WO | WO-2004/045562 A2 | 6/2004 |
| WO | WO-2006/052710 A1 | 5/2006 |
| WO | WO-2006/096626 A2 | 9/2006 |
| WO | WO-2007/014137 A2 | 2/2007 |
| WO | WO-2007/067714 A2 | 6/2007 |
| WO | WO-2007/089934 A2 | 8/2007 |
| WO | WO-2008/048711 A1 | 4/2008 |
| WO | WO-2008/144394 A2 | 11/2008 |
| WO | WO-2009/009083 A1 | 1/2009 |
| WO | WO-2009/023567 A1 | 2/2009 |
| WO | WO-2010/011619 A1 | 1/2010 |
| WO | WO-2010/107457 A1 | 9/2010 |
| WO | WO-2010/141666 A2 | 12/2010 |
| WO | WO-2011/119605 A2 | 9/2011 |
| WO | WO-2012/018872 A1 | 2/2012 |
| WO | WO-2012027359 A1 | 3/2012 |
| WO | WO-2012/088494 A1 | 6/2012 |

OTHER PUBLICATIONS

Alkermes: "Strong Results for Alkermes' ALKS 5461 in Major Depressive Disorder," Retrieved from the internet: URL: http//www.thepharmaleter.com/file/109997/strong-results-for-alkermes-alks-5461-in-major-depressive-disorder. Html, retrieved on Mar. 14, 2013 (Jan. 2012).

Alpharma Pharmaceuticals, AL0-01 (Morphine Sulfate Extended-Release with Sequestered Naltrexone Hydrochloride) Capsules for the Management of Moderate to Severe Pain when a Continuous, Around-the-Clock Opioid Analgesic is Needed for an Extended Period of Time, Meeting of the Anesthetic and Life Support Drugs Advisory Committee, Open Session-Briefing Package, pp. 1-123, Nov. 14, 2008.

Anonymous: "A Phase 3 Study to Evaluate Weight Gain of ALKS 3831 Compared to Olanzapine in Adults with Schizophrenia", ClinicalTrials.gov, Sep. 18, 2018 (Sep. 18, 2018), pp. 1-112, XP055890034.

Baptista, T., et al., "Naltrexone does not prevent the weight gain and hyperphagia induced by the antipsychotic drug sulpiride in rats," Appetite, 34, pp. 77-86 (2000).

Beletsky, L., et al., "Physicians' Knowledge of and Willingness to Prescribe Naloxone to Reverse Accidental Opiate Overdose: Challenges and Opportunities," Journal of Urban Health: Bulletin of the New York Academy of Medicine, 84 (1 ): pp. 126-136 (Dec. 2006).

Bell, J., et al., Clinical Guidelines and Procedures for the Use of Naltrexone in the Management of Opioid Dependence, Australia, pp. 1-57 (Aug. 2003).

Belluzzi, J.D., et al., "Enkephalin May Mediate Euphoria and Drive-Reduction Reward," Nature, 266, pp. 556-558 (Apr. 1977).

Berge, et al. "Pharmaceutical Salts"; 1977; Journal of Pharmaceutical Sciences; 66(1 ): 1-19.

Bianchetti, et al., "Quaternary Derivatives of Narcotic Antagnoists: Stereochemical Requirements at the Chiral Nitrogen for in vitro and in vivo Activity," Life Sciences, 33 (Suppl 1), pp. 415-418 (1983).

Bianchi, et al., "Quaternary Narcotic Antagonists' Relative Ability to Prevent Antinociception and Gastrointestinal Transit Inhibition in Morphine-Treated Rats as an Index of Peripheral Selectivity," Life Sciences 30(22): pp. 1875-1883 (1982).

Bidlack, et. al., 8-Carboxamidocyclazocine: a long-acting, novel benzomorphan, J Pharmacal Exp Ther. Jul. 2002; 302(1 ):374-80.

Bodnar, R., "Preclinic Effects of Opioid Antagonists on Feeding and Appetite," Opiate Receptors and Antagonists: From Bench to Clinic, Dean, Reginald, et al., Human Press pp. 387-406 (Jan. 2009).

(56) References Cited

OTHER PUBLICATIONS

Cacchi, et al., "Palladium-Catalyzed Carbonylation of Aryl Triflates," Tetrahedron Ltrs., 27, pp. 3931-3934 (1996).

Cao, et al., "Why is it Challenging to Predict Intestinal Drug Absorption and Oral Bioavailability in Human Using Rat Model," Pharmaceutical Research, 23(8), pp. 1675-1686 (Aug. 2006).

Clarke, S., et al., "Naloxone in Opioid Poisoning: Walking the Tightrope," Emergency Medicine Journal, 2005, vol. 22, pp. 612-616.

Cone, EJ. et al. Fluorescence Properties of Pseudomorphine and Congeners: Structure-Activity Relationships. Journal of Pharmaceutical Sciences. 1980, vol. 69, p. 254.

Coop et al, "? Opioid Affinity and Selectivity of 4-Hydroxy-3-methoxyindolomorphianan Analogues Related to Naltrindole," J. Med. Chem. 42, 1673-1679 (1999).

Coop et al, "Direct and Simple Conversion of Codeine to Thebainone-A and Dihydrothebainone", Heterocycles 50, 39-42 (1999).

Correll et al, "Effects of olanzapine combined with samidorphan on weight gain in schizophrenia: a 24-week phase 3 study," Am J Psychiatry, 2020, 177(12): 1168-1178.

Cunningham et al., "Samidorphan miligates olanzapine-induced weight gain and metabolic dysfunction in rats and non-human primates," Journal of Psychopharmacology, 2019, 1-14.

Danso-Danquah et al. "Synthesis and ? Binding Proteins of 2'-Substituted . . . " J. Med. Chem. 38, 2978-2985 (1995).

Danso-Danquah, et al., "Synthesis and o Binding Properties of 2' Substituted," J. Med. Chem., 38, 2978-2985 (1995).

Davies et al. "Palladium catalysed elaboration of codeine and morphine" J. Chem. Soc., Perkin Trans. 1, 1413-1420 (2001).

Davoodi et al., "Hyperphagia and increased meal size are responsible for weight gain in rats treated sub-chronically with olanzapine," Psychopharmacology, 2009, 203: 693-702.

Diaz, et. al., SAR and biological evaluation of novel trans-3,4-dimethyl-4-arylpiperidine derivatives as opioid antagonists, Bioorg Med Chem Lett. Sep. 1, 2005;15(17):3844-8.

Dorwald, F., Zaragoza "Side Reactions in Organic Synthesis," Wiley-VCH, Weinheim p. IX of Preface (2005).

Elman, I., et al., "Food Intake and Reward Mechanisms in Patients in Schizophrenia: Implications for Metabolic Disturbances and Treatment with Second-Generation Antipsychotic Agents," Neuropsychopharmacology 31, pp. 2091-2120 (2006).

Faulkner et al. "Interventions to Reduce Weight Gain in Schizophrenia" (Schizophrenia Bulletin 33(3) 654-656 (2007).

Garriock, H.A., et al., "Association of Mu-Opioid Receptor Variants and Response to Citalopram Treatment in Major Depressive Disorder," Am. J. Psychiatry 167(5): pp. 565-573 (May 2010).

Greenway, F., et al., "Effect of Naltrexone Plus Bupropion on Weight Loss in Overweight and Obese Adults (COR-I): a Multicentre, Randomised, Double-Blind, Placebo-Controlled, Phase 3 Trial," The Lancet Limited, 376 (9741); pp. 595-605 (2010).

Heiner et al. "Efficient Kg-Scale Synthesis of Thrombin Inhibitor CRC 220," Tetrahedron, vol. 51, No. 44, pp. 12047-12068 (1995).

Huidobro-Toro, et al., Comparative Study on the effect of Morphine and the opioid-like pepties in the vas deferens of rodents: Species and strain differences, evidence for multiple opiate receptors, Life Sciences vol. 28, pp. 1331-1336 (1981).

Ida, The Nonnarcotic Antitussive Drug Dimemorfan: A Review., Clin Ther. Mar.-Apr. 1997 19(2):215-31.

International Preliminary Examination Report for PCT/US01/45581, date of completion Feb. 5, 2003.

International Search Report and Written Opinion for PCT/US2009/051200, dated Nov. 11, 2009.

International Search Report and Written Opinion from International Application No. PCT/US2008/072632, dated Dec. 23, 2008.

International Search Report and Written Opinion from International Application No. PCT/US2011/029425, dated Sep. 16, 2011.

International Search Report and Written Opinion from International Search Authority for PCT/US2008/063713, dated May 28, 2009.

International Search Report and Written Opinion dated Apr. 19, 2022, for International Application No. PCT/EP2021/081585 filed Nov. 12, 2021 (28 pages).

International Search report for PCT/US01/45581, date of completion Jul. 30, 2022.

International Search Report from International Application No. PCT/US2006/028634, dated Jan. 26, 2007.

International Search report from Internationl Application No. PCT/US2005/039911, date of completion Apr. 19, 2006.

Invitation to Provide Informal Clarification dated Feb. 18, 2022, for International Application No. PCT/EP2021/081585 filed Nov. 12, 2021 (10 pages).

IPRP for International Application No. PCT/US2006/028634, dated Jan. 22, 2008.

Isseroff, R.G., et al., "Regionally Selective Increases in 1-1 Opioid Receptor Density in the Brains of Suicide Victims," Brain Research 530, pp. 312-316 (1990).

Jarusuraisin, "Opioid antagonists for alcohol dependence." The Cochrane Database of Systemic Reviews, Issue. Art. No.: CD001867. DOI: 10.1 002/14651858.CD001867. Apr. 22, 2002, pp. 1-44.

Jendralla, et al., "Efficient Kg-Scale Synthesis of Thrombin Inhibitor CRC 200," Tetrahedron vol. 51, No. 44 pp. 12047-12068 (1995).

Kennedy, S.E., et al., "Dysregulation of Endogenous Opioid Emotion Regulation Circuitry in Major Depression in Women," Arch Gen Psychiatry 63, pp. 1199-1208 (Nov. 2006).

Ko, MC et al., "Differentiation of kappa opioid-agonist-induced antinociception by naltrexone apparent pA2 analysis in rhesus monkeys," J Pharmacol Exp Ther. May 1998;285(2):518-26.

Kubota et al. "Palladium-Catalyzed Cyanation of Hindered, Electron-Rich Aryl Triflates by Zinc Cyanide" Tetrahedron LTrs. 39, 2907-2910.

Kubota et al. "Synthesis and Biological Activity of 3-Substituted . . . " Bior. Med. Chem. Ltrs. 8, 799-804 (1998).

McCurdy et al., "Investigation of Phenolic Bioisosterism in Opiates: 3-Sulfonamido Analogues of Naltrexone and Oxymorphone," Org. Lett. 2, 819-821 (2000).

Mohasci et al., Acylmorphinans. A Novel Class of Ptent Analgesic Agents, Journal of Medicinal Chemistry, 1985, 28(9) 1177-80.

Morera, et al., "A Palldium-catalyzed carbonylative route to primary amides," Tetrahedron Ltrs. 39, pp. 2835-2838 (1998).

Nagata, H. et al. A concise route to (−)-morphine. ChemComm. 2001, p. 1094, scheme 2.

Naltrexone Hydrochloride—(naltrexone hydrochloride tablet, film coated, Accord Healthcare, Inc., Feb. 2001).

Nan Bhargava et al., Synthesis of 2'-Amino-17-cyclopropylmethyl-6,7-dehydro-3,14-dihydroxy-4,5?-eposy-6,7:4'6'-thiazolomorphinan from Naltrexone[1], J. Heterocyclic Chem. 34, 1195-1203 (1997).

Neumeyer, et al, "Design and Synthesis of Novel Dimeric Morphinan Ligands for ? and ? Opioid Receptors," J. Med. Chem. 46, 5162-5170 (2003).

Opioid Overdose, Best Practice, BMJ Evidence Centre, retrieved from the Internet http://bestpractice.bjm.com, Feb. 12, 2013.

OTC Pharm Instructions: Naltrexone Hydrochloride Tablet: http://otc-med-pharm.com/buy_revia_en-us.html? sub=1968&otc=naltrexo (Oct. 2013).

Pathak Sanjeev et al: "Potential of Samidorphan: A Phase I, Oxycodone-, Pentazocine-, Naltrexone-, and Placebo-Controlled Study." J Clin Pharmacol. Feb. 2019;59(2):218-228. doi: 10.1002/jcph.1343. Epub Nov. 26, 2018. PMID: 30476361.

Plodkowski RA, et al., "Bupropion and naltrexone: a review of their use individually and in combination for the treatment of obesity," Expert Opin Pharmacother. Apr. 2009;10(6):1069-81.

Preda, A., Opioid Abuse Treatment & Management, Medscape Drugs, Diseases and Procedures, http://emedicine.medscape.com/article/287790-treatment (Oct. 2013).

Pub Chern CID 15586509, Created Feb. 12, 2007; Retrieved Sep. 2, 2011 (http://pubchem.ncbi.nlm.nih.gov/ summary/summary.cgi? cid= 15586506&loc=ec res).

Pub Chern CID 15974736, Created Mar. 14, 2007; Retrieved Jun. 22, 2011 (http://pubchem.ncbi.nlm.nih.gov/summary/ summary.cgi? cid= 1597 4 736).

(56) References Cited

OTHER PUBLICATIONS

Pub Chern CID 16667612, Created Aug. 16, 2007; Retrieved Sep. 2, 2011 (http://Qubchem.ncbi.nlm.nih.gov/ summary/summmyy.cgi?cid= 16667612&loc=ec res).
Redfern, N., "Dihydrocodeine Overdose Treated with Naloxone Infusion," British Medical Journal, 1983, vol. 287, pp. 751-752.
Rege S. Antipsychotic induced weight gain in schizophrenia:mechanisms and management. Aust N Z J Psychiatry. May 2008;42(5):369-81. doi: 10.1080/00048670801961123. PMID: 18473255.
Remmers, AE. Medzihradsky F. Resolution of biphasic binding of the opioid antagonist naltrexone in brain membranes. J Neurochem. Oct. 1991;57(4):1265-9.
Rennison, D., et al., Structural Determinants of Opioid Activity in Derivatives of 14-Aminomorphinones: Effects of Changes to the Chain Linking of the C14-Amino Group to the Aryl Ring, Journal of Medicinal Chemistry 49(20): pp. 6104-6110 (2006).
Revia—naltrexone hydrochloride table, film coated, Teva Women's Health Inc., pp. 1-10 (Feb. 2009).
Richards, K.L., Opiods: Addiction vs. Dependence, HealthCentral, http://www.healthcentral.com/chronic-pain/coping-279488-5.html (Oct. 2013).
Saal, Christopher, "Pharmaceutical Salts Optimization of Solubility or Even More?," American Pharmaceutical Review, pp. 1-6, http://www.americanpharmaceuticalreview.com/ downloaded Feb. 7, 2013.
Sayre, et. al., Design and Synthesis of Naltrexone-Derived Affinity Labels with Nonequilibrium Opioid Agonist and Antagonist Activities. Evidence for the Existence of Different 1-1 Receptor Subtypes in Different Tissues, J. Medicinal Chemistry, 1984, 27: 1325-1335.
Schultz, et al. 2001, "Opioids and cardioprotection." Pharmacology & Therapeutics, vol. 89, pp. 123-137.
Simpkins, et al., "Evaluation of the Sites of Opioid Influence on Anterior Pituitary Hormone Secetion Using a Quaternary Opiate Antagonist," Neuroendocrinology, 54(4): pp. 384-390 (1991).
Spertus et al., "Risk of weight gain for specific antipsychotic drugs: a meta-analysis," Nature Partner Journals Schizophrenia 4, 2018, 12: 1-7.
Sun Lei et al: "Bioequivalence of Olanzapine Given in Combination With Samidorphan as a Bilayer Tablet (ALKS 3831) Compared With Olanzapine-Alone Tablets: Results From a Randomized, Cross-over Relative Bioavailability Study", Clinical Pharmacology in Drug Development, vol. 8, No. 4, Jul. 30, 2018 (Jul. 30, 2018), pp. 459-466, XP055890158, GB ISSN: 2160-763X, DOI: 10.1002/cpdd.601.
Sun Lei et al: "Pharmacokinetics and Short-term Safety of ALKS 3831, a Fixed-dose Combination of Olanzapine and Samidorphan, in Adult Subjects with Schizophrenia", Clinical Therapeutics, vol. 40, No. 11, Nov. 1, 2018 (Nov. 1, 2018), pp. 1845-1854.e2, XP055890116, Amsterdam, NL ISSN: 0149-2918, DOI: 10.1016/j.clinthera.2018.09.002.
Tada, H., et al., "Ketalisation of alpha, beta-Unsaturated Ketones: Part I 3-Methoxy-N-Methylmorphinan Derivatives and 14-Hydroxycodeinone", Tetrahedron Letters, 10(22): pp. 1805-1808 (1969).
Taylor DM, McAskill R. Atypical antipsychotics and weight gain—a systematic review. Acta Psychiatr Scand. Jun. 2000;101(6):416-32.
Tek, C., et al., "Investigating the safety and efficacy of naltrexone for anti-psychotic induced weight gain in severe metal ilness: study protocol of a double-blind, randomized, placebo-controlled trial," BMC Psychiatry, 13, p. 176 (2013).
Todtenkopf, M., et al., "In vivo Characterization of Novel, Peripherally-Acting Opioid Antagonists," Society for Neuroscience Abstract Viewer and Itinerary Planner, vol. 38, 38th Annual Meeting of the Society-for-Nueroscience, Nov. 2008.
Van Dorp, et al., Naloxone Treatment in Opioid Addiction: The risks and benefits, Expert Opin. Drug Saf 6(2): pp. 125-132 (2007).
Vanalstine, et. al., Redefining the structure-activity relationships of 2,6-methano-3-benzazocines. 5. Opioid receptor binding properties of N-((4'-phenyl)-phenethyl)analogues of 8-CAC, Bioorg Med Chem Lett. Dec. 1, 2007;17(23):6516-20.
Vanalstine, M. Design Synthesis and Evaluation of Novel N-Substituted Derivatives of 8-Carboxamidocyclazocine, Thesis, Rensselaer Polytechnic Institute, 2007.
Varma, et al., "Microwave-Accelerated Solvent-Free Synthesis of Thioketones," Thiolactones, Hioamides, Thionoesters, and Thioflavonoids, Organic Letters, vol. 1, No. 5, pp. 697-700 (1999).
Wells T. Ghrelin—Defender of frat. Prog Lipid Res. Sep. 2009; 48(5):257-74. Epub May 4, 2009.
Wentland et al. "8-Aminocyclazocine Analogues: Synthesis and Structure . . . " Bior. Med. Chem. Ltrs. 10, 183-187 (2000).
Wentland et al. "Selective Protection and Functionalization of Morphine: synthesis and opioid receptor binding properties of 3-amino-3-desoxymorphine derivatives" J. Med. Chem. 43, 3558-3565 (2000).
Wentland et al., "Redefining the structure-activity relationships of 2,6-methano-3-benzazocines. Part 3: 8-thiocarboxamido and 8-thioformamido derivatives of cyclazocince," Bioorg. Med. Chem. Letters. 2005, 15(1): 2547-2551.
Wentland, et al. Redefining the structure-activity relationships of 2,6-methano-3-benzazocines. Part 6: Opioid receptor binding properties of cyclic variants of 8-carboxamidocyclazocine, Bioorg Med Chem. May 15, 2008; 16(1):5653-64.
Wentland, et al., Redefining the structure-activity relationships of 2,6-methano-3-benzazocines. 4. Opioid receptor binding properties of 8-[N-(4'-phenyl)-phenethyl)carboxamido]analogues of cyclazocine and ethylketocycalzocine, J. Med. Chem. Sep. 7, 2006;49 (18): 5635-9.
Wentland, et al., Synthesis and opioid receptor binding properties of a highly potent 4-hydroxy analogue of naltrexone, Bioorg Med Chem Lett. Apr. 15, 2005;15(8):2107-10.
Wentland, et. al., "3-Carboxamido Analogues of Morphine and Naltrexone: Synthesis . . . " Biorg. Med. Chem. Ltrs. 11, 1717-1721 (2001).
Wentland, et. al., "8-Carboxamidocyclazocine Analogues: Redefining the Structure-Activity . . . " Biorg. Med. Chem. Ltrs. 11, 623-626 (2001).
Wentland, et. al., Redefining the structure-activity relationships of 2,6-methano-3-benzazocines. Part 2: 8-formamidocyclazocine analogues, Bioorg Med Chern Lett. Jun. 2, 2003; 13(11 ): 1911-4.
Wentland, et. al., Syntheses and opioid receptor binding properties of carboxamido-substituted opioids, Bioorg Med Chem Lrtt. Jan. 1, 2009;19(1):203-8.
Wentland, et. al., Syntheses of novel high affinity ligands for opioid receptors, Bioorg Med Chem Lett. Apr. 15, 2009; 19(8):2289-94.
Wentland, M. P., et al., "Redefining the Structure-Activity Relationships of 2, 6-methano-3-benzazocines, Part 7: Syntheses and Opioid Receptor Properties of Cyclic Variants of Cyclazocine," Bioorgranic & Medicinal Chemistry Letters, 2009, pp. 365-368 , vol. 19, No. 2.
Wentland, Mark P., et al., "Synthese and Opioid Receptor Binding Affinities of 8-Amino-2,6-methano-3-benzazocines," Journal of Medicinal Chemistry, 2003, pp. 838-849, vol. 46, No. 5.
Written Opinion of International Application No. PCT/US2005/039911, completed Apr. 19, 2006.
Yamamoto, et al., "Buprenorphine Activates 1-1 and Opioid Receptor Like-1 Receptors Simultaneously, but the Analgesic Effect Is Mainly Mediated by 1-1 Receptor Activation in the Rat Formalin Test", Journal of Pharmacology and Experimental Therapeutics, vol. 318, No. 1, pp. 206-213 (2006).
Yuan, C., et al., "Methylnaltrexone Potentiates Body Weight and Fat Reduction with Leptin," Journal of Opioid Management: A medical Journal of Proper and Adequate Use, Weston Medical Publishing, 5(6): pp. 373-378 (No. 2009).
Zaveri, N. et al., Small-Molecule Agonists and Antagonists of the Opioid Receptor-Like Receptor (ORL 1 ,NOP): Ligand-Based Analysis of Structural Factors Influencing Intrinsic Activity at NOP, The AAPS Journal, 2005, E345-E352.
Zhang et al., 10-ketomorphinan and 3-substituted-3-desoxymorphinan analogues as mixed k and u Opioid ligands: synthesis and biological evaluation of their binding affinity at opioid receptors, journal of mediciunal chemistry, 2004, 165-174.

(56) References Cited

OTHER PUBLICATIONS

Zhang J, et al., The mu-opioid receptor subtype is required for the anorectic effect of an opioid receptor antagonist. Eur. J. Pharmacol. Sep. 18, 2006; 545(2-3): 147-52. Epub Jul. 5, 206.

Pathak et al., Abuse potential of samidorphan: A phase I oxycodone-, pentazocine-, naltrexone- and placebo-controlled study, The Journal of Clinical Pharmacology, 2019, 59(2): 218-228.

Sun et al., "Pharmacokinetics short-term safety of alks 3831, a fixed-dose combination of olanzapine and samidorphan, in adult subjects with schizophrenia", Clinical Therapeutics, 2018, 40(11): 1845-1854.

Sun et al., "Bioequivalence of olanzapine given in combination with samidorphan as a bilayer tablet (ALKS 383 I) compared with olanzapine-alone tablets: results from a randomized, crossover relative bioavailability study", Clinical Pharmacology in Drug Development, 2019, 8(4): 459-66.

U.S. Appl. No. 11/266,651, filed Nov. 3, 2005, Issued, U.S. Pat. No. 7,262,298.

U.S. Appl. No. 11/760,039, filed Jun. 8, 2007, Issued, U.S. Pat. No. 8,680,112.

U.S. Appl. No. 14/169,305, filed Jan. 31, 2014, Issued, U.S. Pat. No. 8,802,655.

U.S. Appl. No. 12/903,462, filed Oct. 13, 2010, Issued, U.S. Pat. No. 9,119,848.

U.S. Appl. No. 17/989,869, filed Nov. 18, 2022, Pending.

U.S. Appl. No. 14/297,171, filed Jun. 5, 2014, Issued, U.S. Pat. No. 9,126,977.

U.S. Appl. No. 15/342,263, filed Nov. 3, 2016, Issued, U.S. Pat. No. 9,943,514.

U.S. Appl. No. 14/813,260, filed Jul. 30, 2015, Issued, U.S. Pat. No. 9,517,235.

U.S. Appl. No. 15/923,084, filed Mar. 16, 2018, Issued, U.S. Pat. No. 10,300,054.

U.S. Appl. No. 16/390,531, filed Apr. 22, 2019, Issued, U.S. Pat. No. 10,716,785.

U.S. Appl. No. 16/899,708, filed Jun. 12, 2020, Issued, U.S. Pat. No. 11,185,541.

U.S. Appl. No. 17/071,166, filed Oct. 15, 2020, Issued, U.S. Pat. No. 11,351,166.

U.S. Appl. No. 17/071,236, filed Oct. 15, 2020, Issued, U.S. Pat. No. 11,241,425.

U.S. Appl. No. 17/505,896, filed Oct. 20, 2021, Pending.

U.S. Appl. No. 17/855,242, filed Jun. 30, 2022, Allowed.

\* cited by examiner

IMMEDIATE RELEASE MULTILAYER TABLET

CROSS-REFERENCE

This application is a continuation of U.S. patent application Ser. No. 17/855,242, filed Jun. 30, 2022, which is a continuation of International Application Number PCT/EP2021/081585 filed Nov. 12, 2021, which claims priority to U.S. Provisional Application No. 63/113,067 filed Nov. 12, 2020, each of which is incorporated herein by reference in its entirety.

BACKGROUND

Antipsychotic medications are among the most important therapeutic tools for treating various psychotic disorders. There are two categories of antipsychotics, typical and atypical. Typical antipsychotics e.g., haloperidol and chlorpromazine, were first developed in the 1950's and were used to treat psychosis, particularly schizophrenia. Common side effects of typical antipsychotics include: dry mouth, tremors, weight gain, muscle tremors, and stiffness. In addition, typical antipsychotics yield extrapyramidal side effects. These side effects include: motor disturbances, parkinsonian effects, akathesia, dystonia, akinesia, tardive dyskinesia, and neuroleptic malignant syndrome. Some of these side effects have been described to be worse than the actual symptoms of schizophrenia. Atypical antipsychotics are considered to be the first line of treatment for schizophrenia because of the improved extrapyramidal side effect profile in comparison to typical antipsychotics. Atypical antipsychotics are also associated with superior tolerability, adherence and relapse prevention and have led to improved treatment for patients with serious mental illness.

However, antipsychotics are also associated with significant weight gain. Clinical studies have reported that 40-80% of patients under chronic atypical antipsychotic treatment experience substantial weight gain, e.g., exceeding their ideal body weight by 20%, and increases the risk of obesity. Weight gain was found to be greatest with clozapine, olanzapine, risperidone, and quetiapine, and less with aripiprazole and ziprasidone. Obesity is a leading cause of mortality as it frequently leads to conditions such as diabetes and cardiovascular disorders. In addition, where atypical antipsychotics are increasingly prescribed to children and adolescents with psychiatric disorders, young children who take antipsychotics risk long term health risks associated with rapid weight gain, for example, metabolic changes that could lead to diabetes, hypertension and other illnesses.

Olanzapine is 2-methyl-4-(4-methyl-1-piperazinyl)-10H-thieno[2,3-b][1,5]benzodiazepine. The molecular formula of olanzapine is: $C_{17}H_{20}N_4S$ and the molecular weight is 312.44 g/mol. It is a yellow crystalline powder and has pKa values of 7.80 and 5.44. The chemical structure is:

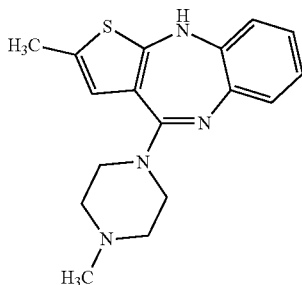 [SMILES: Cc1cc2c(s1)Nc1ccccc1N=C2N1CCN(C)CC1]

Samidorphan is an opioid antagonist (also known as 3-carboxamido-4-hydroxynaltrexone) that preferentially acts as an antagonist of the μ-opioid receptor. Samidorphan L-malate is morphinan-3-carboxamide, 17-(cyclopropylmethyl)-4, 14-dihydroxy6-oxo-, (2S)-2-hydroxybutanedioate. The molecular formula of samidorphan L-malate is $C_{21}H_{26}N_2O_4 \cdot C_4H_6O_5$ and the molecular weight is 504.54 g/mol. It is a white to off-white crystalline powder and has pKa values of 8.3 (amine) and 10.1 (phenol). The chemical structure is:

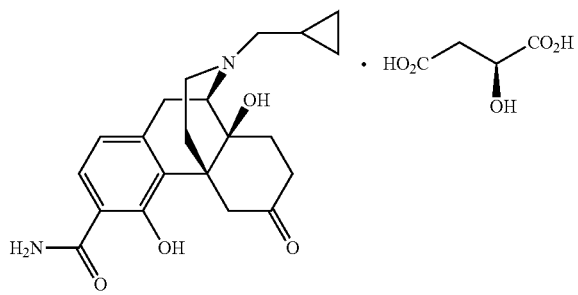 [SMILES: NC(=O)c1ccc2c(c1O)[C@]13CCN(CC4CC4)[C@H](C2)[C@]1(O)CCC(=O)C3 ; O=C(O)C[C@H](O)C(=O)O]

Samidorphan (as Samidorphan L-malate) in combination with olanzapine is marketed by Alkermes as LYBALVI®, which is indicated for the treatment of schizophrenia in adults, bipolar I disorder in adults, acute treatment of manic or mixed episodes as monotherapy and as adjunct to lithium or valproate.

U.S. Pat. No. 10,300,054 discloses a composition comprising samidorphan or derivatives thereof and an antipsychotic including olanzapine.

Therefore, there is a continuing need to develop more effective antipsychotic drug treatments that e.g., reduce weight gain, and that are in easy to use formulations that minimize the need for significantly multiple tablets for administration.

SUMMARY

Described herein, in part, are tablets (e.g., immediate release multi-layer tablets such as bi-layer tablets) for orally delivering olanzapine and samidorphan for treatment of psychotic and other disorders as described herein. Disclosed compositions, e.g., disclosed tablets, that include samidorphan and its associated pharmaceutically acceptable salts, together with olanzapine can provide a once-daily, oral atypical antipsychotic therapeutics that provides the efficacy of olanzapine while mitigating olanzapine-associated weight gain, This disclosure, in part, is directed to tablets that provide a substantially immediate release profile upon administration to a patient but include both samidorphan and olanzapine. For example, although olanzapine may be susceptible to degradation in the presence of samidorphan (e.g., olanzapine and samidorphan are chemically incompatible, this disclosure is directed in part to multi-layer tablets having both olanzapine and samidorphan in a unit formulation that also provides reduced related impurities formation (for example, under typical storage conditions (e.g., 25° C./60% relative humidity and 40° C./75% relative humidity), and can release both samidorphan and olanzapine substantially quickly once administered.

Multi-layer tablets as disclosed herein have the advantage of facilitating simultaneous administration to patients, in need thereof therapeutically effective combinations of olanzapine and samidorphan. The disclosure contemplates multi-layer tablets as well as a bilayer tablet comprising one olanzapine containing layer and one samidorphan (or a pharmaceutically acceptable salt thereof) containing layer, which may be preferred as it simplifies the production process. Multi-layer fixed dose combination tablets comprising of olanzapine and samidorphan (or the equivalent of a pharmaceutically acceptable salt thereof) which have been found to be particularly useful are those comprising a first layer having about 10 mg or 20 mg of samidorphan (or salt thereof e.g. 13.6 mg or 27.2 mg of samidorphan L-malate), and a second layer having between 2.5 mg and about 20 mg of olanzapine, preferably about 2.5 mg, 5 mg, 10 mg, 15 mg or 20 mg of olanzapine. Multilayer tablets of the present invention may optionally comprise a barrier layer of inert material between respective layers of samidorphan and olanzapine. Such a barrier layer serves to maintain physical distance between the active ingredient and prevent their interaction or mixing.

Apart from the active ingredients, olanzapine and samidorphan, tablets of the invention may comprise pharmaceutically acceptable excipients which confer advantages in terms of processability, stability of the dosage form and/or aiding release of active ingredient(s) from the dosage form. Each layer may separately comprise pharmaceutically acceptable excipients such as: diluents, glidants, disintegrants and lubricants. Preferred excipients include microcrystalline cellulose, crospovidone (also known as polyvinyl pyrrolidone or PVP), lactose (anhydrous or hydrates), silicon doxide and magnesium stearate, used separately or in combinations. Additional preferred excipients are described below. It is preferable, although not required, for the same excipients to be used in each active ingredient containing layer of the tablet.

For example, described herein as an embodiment is a pharmaceutically acceptable coated immediate release bilayer tablet for orally delivering olanzapine and 10 mg of samidorphan as a fixed dose, comprising: a first tablet layer comprising 10 mg samidorphan or a pharmaceutically acceptable salt of samidorphan in an amount to deliver 10 mg Samidorphan, about 30-45 wt % microcrystalline cellulose, based on the weight of the first tablet layer, about 35-50 wt % lactose or a hydrate thereof, based on the weight of the first tablet layer; and about 0.5 to about 2 wt % magnesium stearate, a second tablet layer comprising: a dose of olanzapine selected from the group consisting of 2.5 mg, 5 mg, 10 mg, 15 mg and 20 mg of the olanzapine, about 35-45 wt % microcrystalline cellulose, based on the weight of the second tablet layer, about 45-55 wt % lactose or a hydrate thereof, based on the weight of the second tablet layer; and about 1.0 wt % magnesium stearate, and a film coating over the first and second tablet layer.

Also described herein as an embodiment is a pharmaceutically acceptable coated immediate release bilayer tablet for orally delivering olanzapine and 10 mg of samidorphan as a fixed dose, comprising: a first tablet layer comprising:10 mg samidorphan or a pharmaceutically acceptable salt of samidorphan (e.g., samidorphan L-malate) in an amount to deliver 10 mg samidorphan; about 35-43 wt % microcrystalline cellulose, based on the weight of the first tablet layer; about 37-43 wt % lactose or a hydrate thereof, based on the weight of the first tablet layer; and about 1.5 to about 2 wt % magnesium stearate; a second tablet layer comprising: a dose of olanzapine selected from the group consisting of 5 mg, 10 mg, 15 mg and 20 mg of the olanzapine; about 38-42 wt % microcrystalline cellulose, based on the weight of the second tablet layer; about 46-49 wt % lactose or a hydrate thereof, based on the weight of the second tablet layer; and about 1.0 wt % magnesium stearate; and a film coating over the first and second tablet layer.

Also provided for herein is a pharmaceutically acceptable coated immediate release bilayer tablet for orally delivering olanzapine (e.g., 2.5 mg, 5 mg, 10 mg, 15 mg or 20 mg olanzapine), together with 10 mg of samidorphan as a fixed dose, comprising: a first tablet layer comprising: 13.6 mg samidorphan L-malate; about 40 wt % microcrystalline cellulose, based on the weight of the first tablet layer; about 42 wt % lactose monohydrate, based on the weight of the first tablet layer; and about 1.75 wt % magnesium stearate; a second tablet layer comprising: a dose of olanzapine, for example, a dose of olanzapine selected from the group consisting of 2.5 mg, 5 mg, 10 mg, 15 mg and 20 mg of the olanzapine; about 40 wt % microcrystalline cellulose, based on the weight of the second tablet layer; about 47 wt % lactose or a hydrate thereof, based on the weight of the second tablet layer; and about 1.0 wt % magnesium stearate; and a film coating over the first and second tablet layer.

In one embodiment, described herein is a pharmaceutically acceptable coated immediate release bilayer tablet for orally delivering olanzapine and samidorphan (e.g., 10 mg of samidorphan) together as a fixed dose, comprising: a first tablet layer (for example, having 10 mg samidorphan, or a pharmaceutically acceptable salt of samidorphan (e.g., samidorphan L-malate) in an amount to deliver 10 mg samidorphan); and a second tablet layer having, for example, 2.5 mg, 5 mg, 10 mg, 15 mg or 20 mg of olanzapine, and a film coating; wherein the tablet releases at least 80% of both the olazanpine and the samidorphan after 15 minutes when the tablet is tested in 500 mL USP acetate buffer at pH 4.5 using a USP Apparatus II (Paddle Method) at 37° C., with a paddle speed of 75 rpm and using a three-prong sinker.

In another embodiment, described herein is a pharmaceutically acceptable coated immediate release bilayer tablet for orally delivering olanzapine and 10 mg of samidorphan together as a fixed dose, comprising: a first tablet layer having 10 mg samidorphan, or a pharmaceutically acceptable salt of samidorphan in an amount to deliver 10 mg samidorphan; and a second tablet layer having 5 mg, 10 mg, 15 mg or 20 mg of olanzapine, and a film coating; wherein the tablet releases at least 85% of both the olazanpine and the samidorphan after 15 minutes or after 30 minutes when the tablet is tested in 500 mL 0.1N hydrochloric acid at pH 1.0 using a USP Apparatus II (Paddle Method) at 37° C., with a paddle speed of 75 rpm and using a three-prong sinker.

An exemplary preferred pharmaceutically acceptable coated immediate release bilayer tablet for orally delivering olanzapine and 10 mg or 20 mg of samidorphan as a fixed dose is provided that includes: a first tablet layer comprising: 10 mg or 20 mg samidorphan or a pharmaceutically acceptable salt of samidorphan in an amount to deliver 10 mg or 20 mg samidorphan; about 30-50 wt % microcrystalline cellulose, based on the weight of the first tablet layer; about 35-50 wt % lactose or a hydrate thereof, based on the weight of the first tablet layer; optionally about 3.0 to about 7.0 wt % crospovidone; optionally about 0.5 to about 1.5 wt % colloidal silica; and about 1.5 to about 2.5 wt % magnesium stearate; a second tablet layer comprising: a dose of olanzapine selected from the group consisting of 2.5 mg, 5 mg, 10 mg, 15 mg and 20 mg of the olanzapine; about 30-50 wt % microcrystalline cellulose, based on the weight of the second tablet layer; about 35-50 wt % lactose monohydrate, based on the weight of the second tablet layer; optionally about 3.0 to about 7.0 wt % crospovidone; optionally about 0.5 to about 1.5 wt % colloidal silica; and about 0.5 to about 1.25 wt % magnesium stearate; and a film coating over the first and second tablet layer.

Another exemplary preferred tablet described herein is a pharmaceutically acceptable coated immediate release bilayer tablet for orally delivering 5 mg olanzapine and 10 mg of samidorphan as a fixed dose, comprising: 5 mg olanzapine; 13.62 mg samidorphan L-malate; 60 mg microcrystalline cellulose; 65.88 mg lactose monohydrate; 2.5 mg crospovidone; 0.75 mg colloidal silicon dioxide; 2.25 mg magnesium stearate; and a film coating.

In one preferred embodiment, described herein is a pharmaceutically acceptable coated immediate release bilayer tablet for orally delivering 10 mg olanzapine and 10 mg of samidorphan as a fixed dose, comprising: 10 mg olanzapine; 13.62 mg samidorphan L-malate; 80 mg microcrystalline cellulose; 89.63 mg lactose monohydrate; 3.0 mg crospovidone; 1.0 mg colloidal silicon dioxide; 2.75 mg magnesium stearate; and a film coating.

In another preferred embodiment, described herein is a pharmaceutically acceptable coated immediate release bilayer tablet for orally delivering 15 mg olanzapine and 10 mg of samidorphan as a fixed dose, comprising: 15 mg olanzapine; 13.62 mg samidorphan L-malate; 100 mg microcrystalline cellulose; 113.38 mg lactose monohydrate; 3.5 mg crospovidone; 1.25 mg colloidal silicon dioxide; 3.25 mg magnesium stearate; and a film coating.

In another preferred embodiment, described herein is a pharmaceutically acceptable coated immediate release bilayer tablet for orally delivering 20 mg olanzapine and 10 mg of samidorphan as a fixed dose, comprising: 20 mg olanzapine; 13.62 mg samidorphan L-malate; 120 mg microcrystalline cellulose; 137.13 mg lactose monohydrate; 4.0 mg crospovidone; 1.5 mg colloidal silicon dioxide; 3.75 mg magnesium stearate; and a film coating.

In another preferred embodiment, described herein is a pharmaceutically acceptable coated immediate release bilayer tablet for orally delivering olanzapine and 20 mg of samidorphan as a fixed dose, comprising: a first tablet layer comprising: 20 mg samidorphan or a pharmaceutically acceptable salt of samidorphan in an amount to deliver 20 mg samidorphan; about 35-43 wt % microcrystalline cellulose, based on the weight of the first tablet layer; about 37-43 wt % lactose or a hydrate thereof, based on the weight of the first tablet layer; and about 0.5 to about 2 wt % magnesium stearate; a second tablet layer comprising: a dose of olanzapine selected from the group consisting of 2.5 mg, 5 mg, 10 mg, 15 mg and 20 mg of the olanzapine; about 38-42 wt % microcrystalline cellulose, based on the weight of the second tablet layer; about 46-49 wt % lactose or a hydrate thereof, based on the weight of the second tablet layer; and about 0.5 to about 1.5 wt % magnesium stearate; and a film coating over the first and second tablet layer.

In one embodiment, described herein is a pharmaceutically acceptable coated immediate release bilayer tablet for orally delivering olanzapine and 10 mg of samidorphan as a fixed dose, comprising: a first tablet layer comprising: 10 mg samidorphan or a pharmaceutically acceptable salt of samidorphan in an amount to deliver 10 mg samidorphan; about 35-43 wt % microcrystalline cellulose, based on the weight of the first tablet layer; about 37-43 wt % lactose or a hydrate thereof, based on the weight of the first tablet layer; and about 1.5 to about 2 wt % magnesium stearate; a second tablet layer comprising: a dose of olanzapine selected from the group consisting of 5 mg, 10 mg, 15 mg and 20 mg of the olanzapine; about 38-42 wt % microcrystalline cellulose, based on the weight of the second tablet layer; about 46-49 wt % lactose or a hydrate thereof, based on the weight of the second tablet layer; and about 1.0 wt % magnesium stearate; and a film coating over the first and second tablet layer; wherein the tablet releases at least 85% of olazanpine and at least 85% of the samidorphan after 15 minutes when the tablet is tested in 500 mL USP acetate buffer at pH 4.5 using a USP Apparatus II (Paddle Method) at 37° C., with a paddle speed of 75 rpm and using a three-prong sinker. In a preferred embodiment, olanzapine and samidorphan are released in in vitro testing at pH 1.0 and/or pH 4.5 at substantially the same rate, meaning that the percentage of olanzapine and samidorphan released at across all time points is substantially similar, wherein "substantially" is defined to mean within plus or minus 10%.

In another preferred embodiment, described herein is a tablet having any of the characteristics described above, in which said tablet has a water content of no greater than about 10 wt % of the tablet, no greater than about 9.5 wt % of the tablet, no greater than about 9.0 wt % of the tablet, no greater than about 8.5 wt % of the tablet, no greater than about 8.0 wt % of the tablet, no greater than about 7.5 wt % of the tablet, no greater than about 7.0 wt % of the tablet, no greater than about 6.5 wt % of the tablet, no greater than about 6.0 wt % of the tablet, no greater than about 5.5 wt % of the tablet, no greater than about 5.0 wt % of the tablet, no greater than about 4.5 wt % of the tablet, no greater than about 4.0 wt % of the tablet, no greater than about 3.5 wt % of the tablet, no greater than about 3.0 wt % of the tablet, no greater than about 2.5 wt % of the tablet, no greater than about 2.0 wt % of the tablet, no greater than about 1.5 wt % of the tablet, no greater than about 1.0 wt % of the tablet, no greater than about 0.5 wt % of the tablet, or no greater than about 0.25 wt % of the tablet.

In another preferred embodiment, described herein is a tablet having any of the characteristics described above, in which said tablet has impurities due to olanzapine degradation, samidorphan degradation, or a combination of samidorphan degradation and olanzapine degradation as detected by HPLC, at 6 months, 9 months and/or 12 months or more of storage in a closed container at 25° C. and 60% relative humidity and optionally containing silica gel desiccant, of between about 0.005 wt % and 5.0 wt %, 0.01 wt % and 3.0 wt %, 0.05% and 2.5 wt %, 0.1% and 2.0 wt % and 0.1% to about 1.0 wt %, for example, this includes less than about 1.0 wt %, less than about 0.9 wt %, less than about 0.8 wt %, less than about 0.7 wt %, less than about 0.6 wt %, less than about 0.5 wt %, less than about 0.4 wt %, less than about 0.3 wt %, less than about 0.2 wt %, less than about 0.1 wt %, less than about 0.09 wt %, less than about 0.08 wt %, less than about 0.07 wt %, less than about 0.06 wt %, less than about 0.05 wt %, less than about 0.04 wt %, less than about 0.03 wt %, less than about 0.02 wt %, less than about 0.01 wt %.

Also described herein is a method of preparing a bilayer tablet for oral delivery of olanzapine and samidorphan comprising preparing samidorphan L-malate in a particulate form having a particle size distribution (D10) of between about 10 μm and about 80 μm, a (D50) of between about 40 μm and about 200 μm and a (D90) of between about 100 μm and about 300 μm, more preferably a (D10) of between about 25 μm and about 50 μm, a (D50) of between about 60 μm and about 100 μm and a (D90) of between about 120 μm and about 175 μm. The method further comprises preparing olanzapine having a particle size distribution (D10) of between 10 μm and 100 μm, a D(50) of between 50 μm and 150 μm and a D(90) of between 150 μm and 300 μm, most preferably a D(10) of not less than 22 μm, a D(50) of between 70 µm and 135 µm, and D(90) of not more than 284 µm. A larger particle size distribution of the samidorphan and olanzapine results in a reduced degradation of same due to the reduced surface area. It also reduces the impact of degradation that each active has on the other. For instance, a larger particle size for samidorphan (and resultant reduction in surface area) will result in a reduced mutual degradation effect on the Olanzapine, caused by the samidorphan. However, an excessive increase in particle size of either active ingredient can potentially give rise to poorer flow characteristics and tablet content uniformity. The above particle size range has been observed to lead to reduced degradation whilst at the same time maintaining acceptable flow characteristics for processing purposes.

The samidorphan L-malate particles are charged, along with colloidal silicon dioxide into a first vessel and premixed to form a samidorphan premix. Olanzapine, microcrystalline cellulose, crospovidone, and silicon dioxide are charged into a second vessel and premixed to form an olanzapine premix. The samidorphan and olanzapine premixes are respectively passed through a rotating impeller screening mill. Preferably, the mill has a screen with holes of between about 0.03 to about 0.06 inches (0.762 mm to about 1.524 mm), most preferably between about 0.045 to about 0.055 inches (about 1.14 mm to about 1.4 mm) in diameter. The samidorphan and olanzapine premixes are then blended in bin blenders to form a samidorphan blend and an olanzapine blend. A first and second quantity of magnesium stearate is passed through a screen (most preferably having a hole size of about 350 to 500 microns, most preferably about 425 microns) and added to the samidorphan and olanzapine blends. The samidorphan and olanzapine blends are placed in a tablet press to form a samidorphan and olanzapine blend layers. The aforementioned blend layers are then compressed to form a bilayer tablet. In one embodiment, the compressing of the samidorphan and olanzapine blend layers occurs at a force of between 0.4 kN-2 kN, which ensures an acceptable mechanical strength for the tablet whilst also maintaining the desired release characteristics for the samidorphan and olanzapine in the resultant tablet. The tablet is then coated by applying an aqueous coating suspension to the tablet, and dried for a period of time sufficient such that the water content is less than 5.5 wt % of the tablet. In one embodiment, the drying of the tablet may further comprise selection of the exhaust temperature during coating (preferably maintaining in the range of 42 to 51° C., and most preferably in the range of 43 to 47° C.) and the inlet temperature during drying (preferably in the range of 70 to 80° C., most preferably 75° C.) to aid in achieving the desired water content. Most preferably, a single olanzapine blend composition is used across multiple olanzapine strengths (e.g. 2.5 mg, 5 mg, 10 mg, 15 mg or 20 mg) and the placing of the olanzapine blend into the tablet press includes selecting the weight of olanzapine blend based upon the desired dose of olanzapine in the bilayer tablet, rather than changing the olanzapine blend. Accordingly, a single olanzapine blend formulation can be used to produce multiple olanzapine dosage strengths, such as 2.5 mg, 5 mg, 10 mg, 15 mg or 20 mg of olanzapine which simplifies production of multiple strength tablets. Most preferably, the equipment required to carry out the method is housed in an environment having an ambient temperature of no greater than 25° C. and an ambient relative humidity of no greater than 65% which aids in maintaining a low water content and low level of degradants in the resulting tablet. It is envisaged that such a method could be used to prepare any of the tablet formulations described herein.

The bilayer tablets and associated methods for production and treatment described herein provide a robust solution to the problem of mutual degradation between samidorphan and olanzapine when presented together in a single treatment. The described bilayer tablets provide for release of both actives at substantially the same rate, whilst ensuring that the formulation parameters used to achieve that objective result in a mechanically stable tablet that is not prone to delamination between the samidorphan and olanzapine layers. The blend formulation for olanzapine allows for a single formulation to be useful in creating tablets having multiple olanzapine strengths, and the method for production (particularly the control of the samidorphan and/or olanzapine particle size and the drying of the tablet after coating) ensures that any degradation of the samidorphan or olanzapine due to the ingress of moisture to the tablet is kept at a minimum. This results in a bilayer tablet that is both physically and chemically stable over time, that is simple and convenient to manufacture and that releases olanzapine and samidorphan at a substantially similar rate to ensure optimal delivery of both active ingredients when dosed in vivo.

BRIEF DESCRIPTION OF THE DRAWINGS

In FIGS. 1A-1F, dose strengths shown refer to olanzapine dose/samidorphan dose.

In FIGS. 2A-2F, dose strengths shown refer to olanzapine dose/samidorphan dose.

In FIGS. 3A-3B, dose strengths shown refer to olanzapine dose/samidorphan dose.

DETAILED DESCRIPTION

Figure 1A:
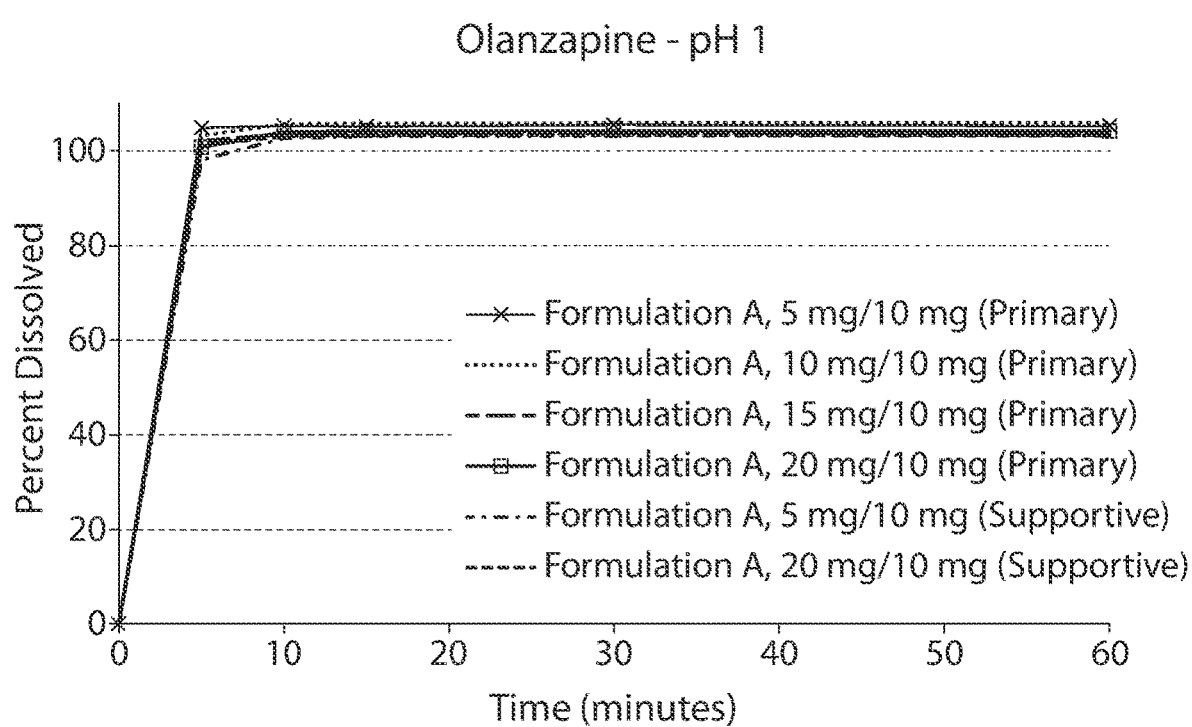
FIG. 1A depicts an exemplary dissolution profile overlay of olanzapine in Formulation A at pH 1.
Figure 1B:
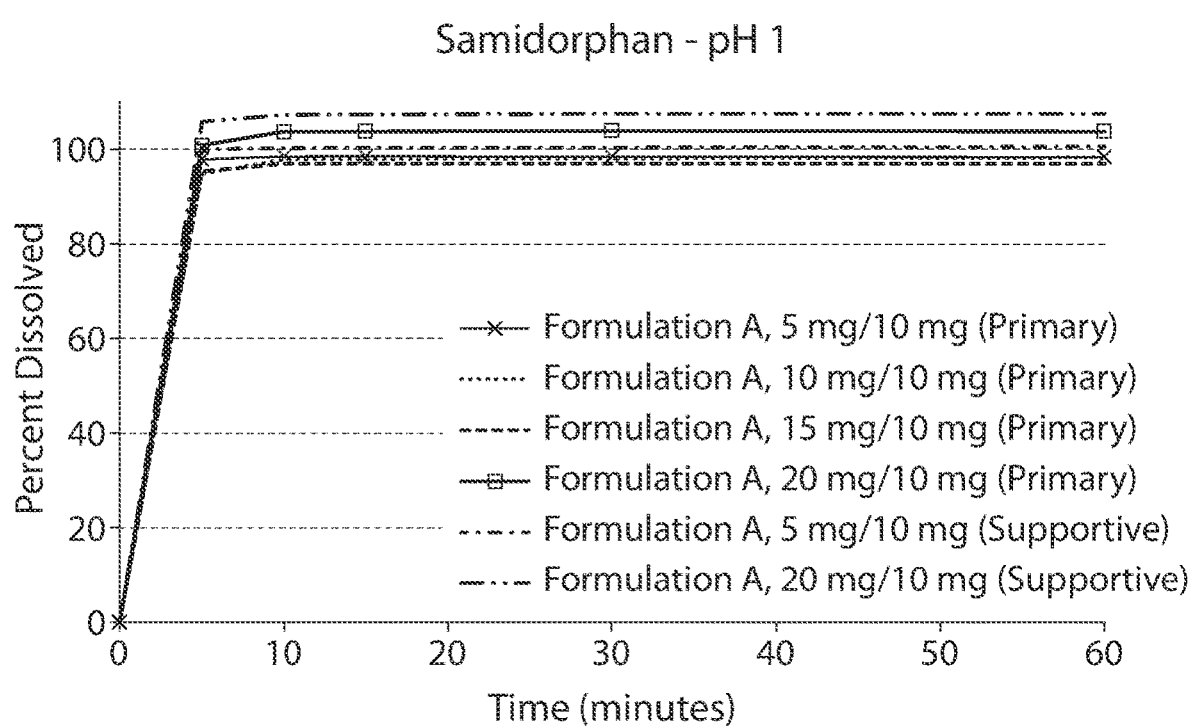
FIG. 1B depicts an exemplary dissolution profile overlay of samidorphan L-malate in Formulation A at pH 1.
Figure 1C:
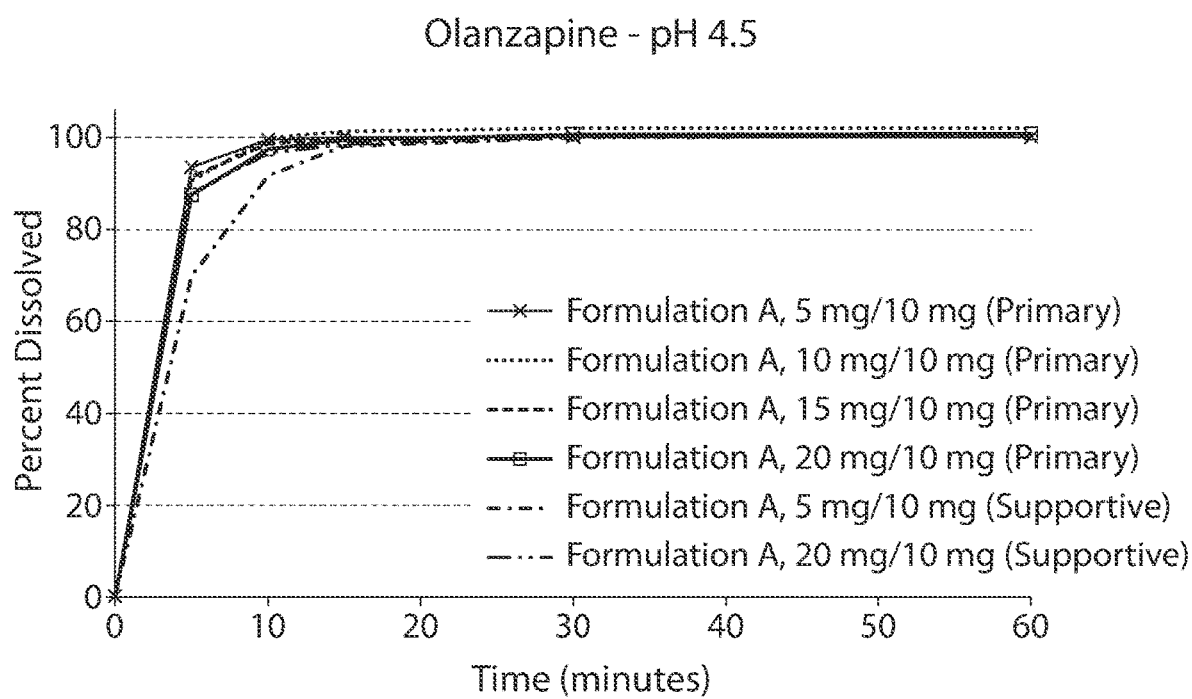
FIG. 1C depicts an exemplary dissolution profile overlay of olanzapine in Formulation A at pH 4.5.
Figure 1D:
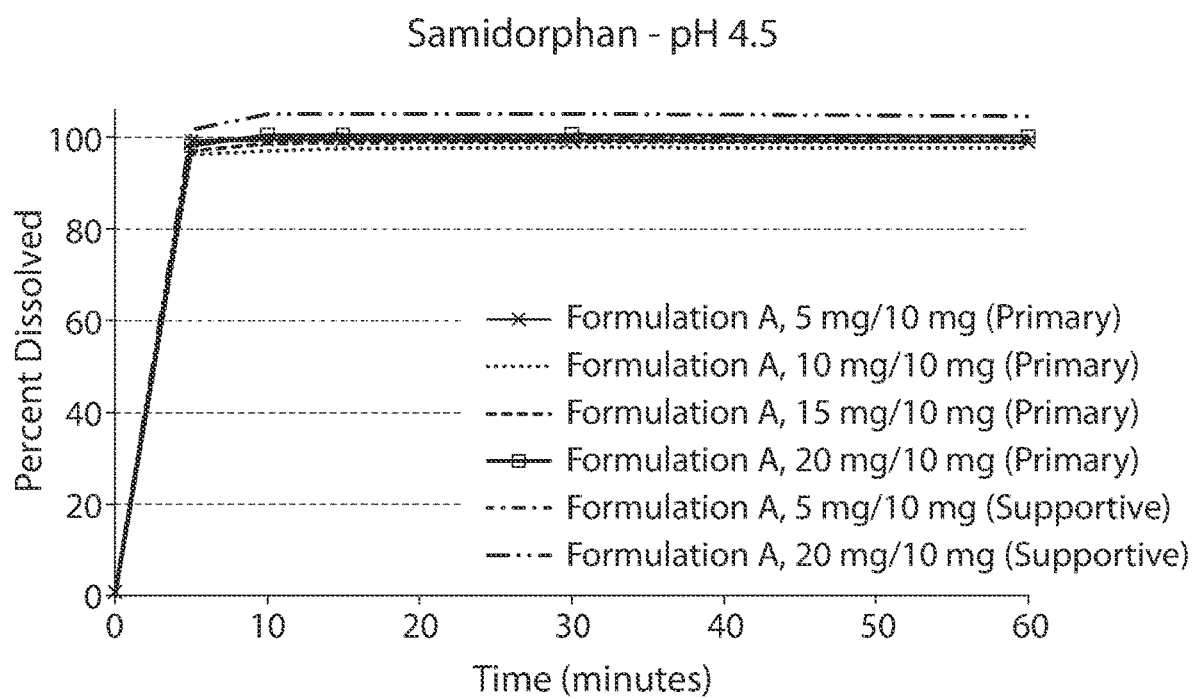
FIG. 1D depicts an exemplary dissolution profile overlay of samidorphan L-malate in Formulation A at pH 4.5.
Figure 1E:
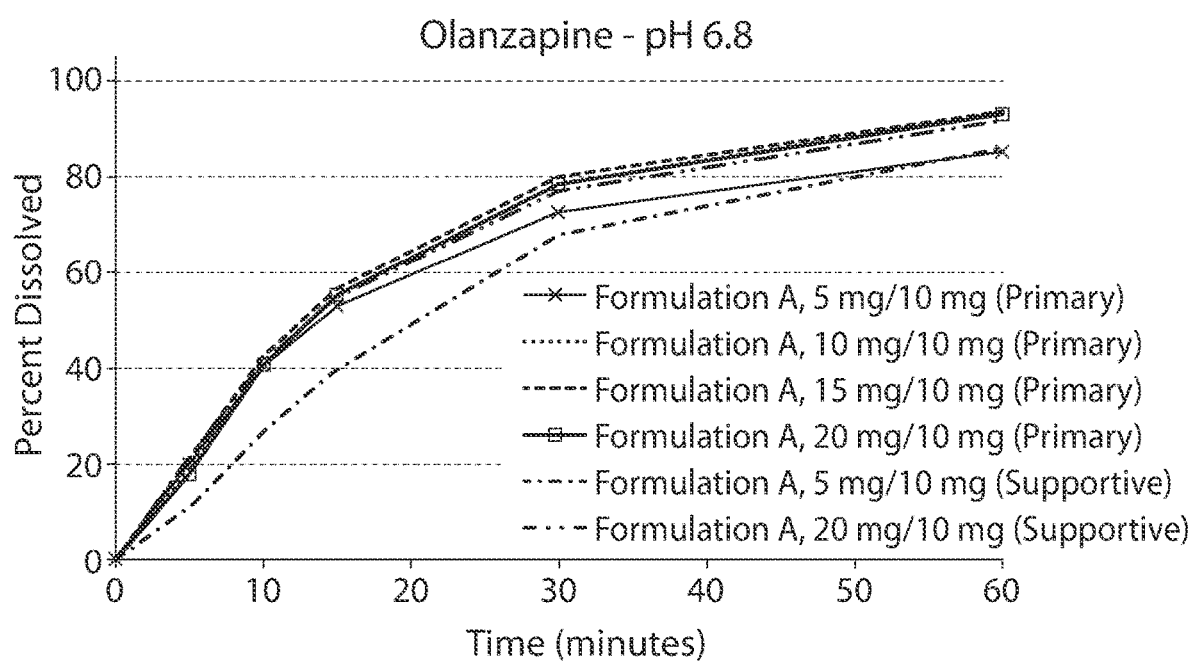
FIG. 1E depicts an exemplary dissolution profile overlay of olanzapine in Formulation A at pH 6.8.
Figure 1F:
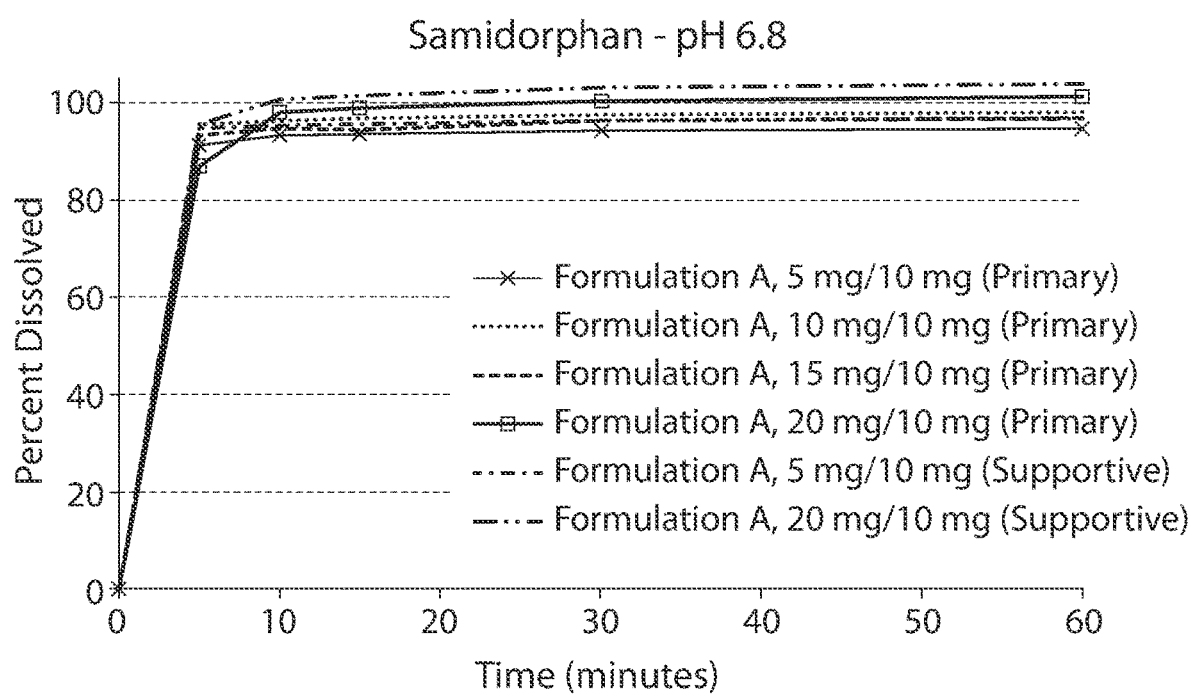
FIG. 1F depicts an exemplary dissolution profile overlay of samidorphan L-malate in Formulation A at pH 6.8.
Figure 2A:
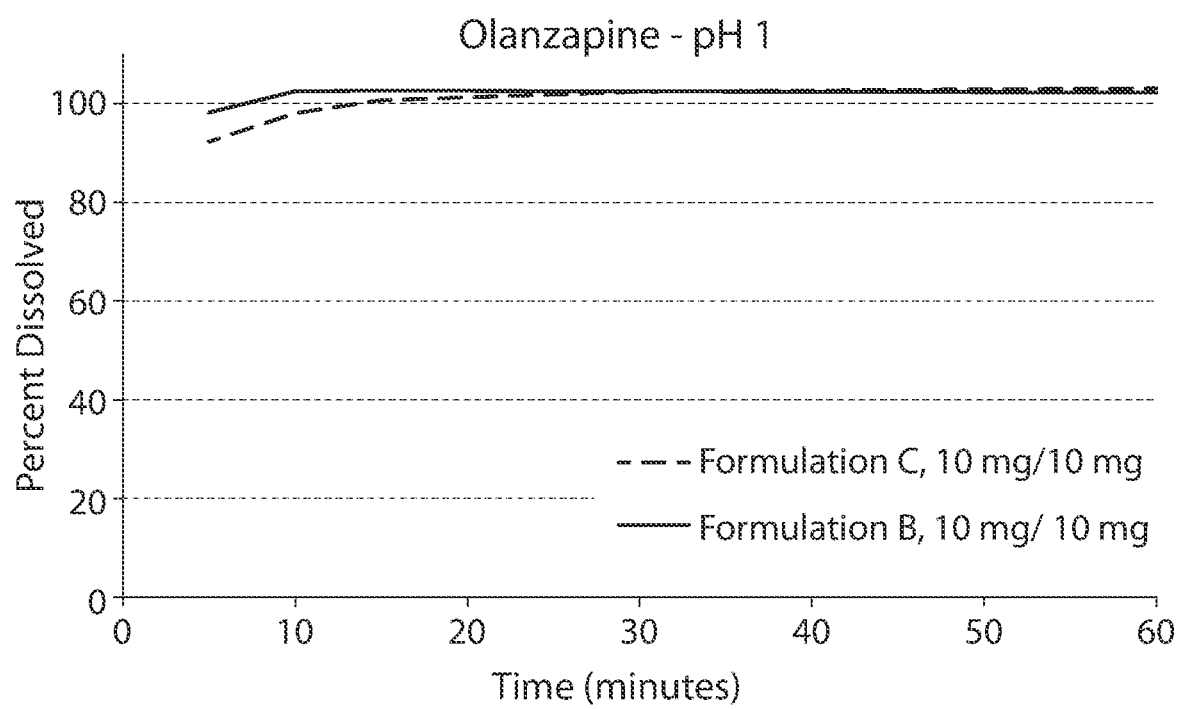
FIG. 2A depicts an exemplary dissolution profile overlay of olanzapine in Formulations B and C at pH 1.
Figure 2B:
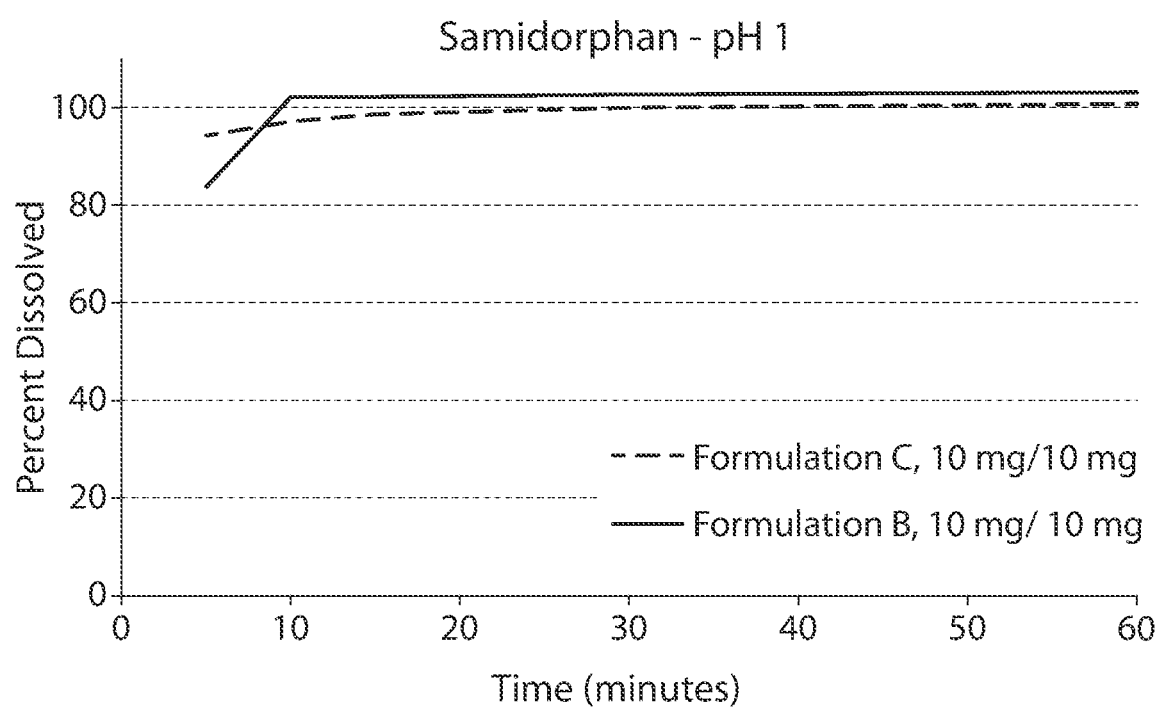
FIG. 2B depicts an exemplary dissolution profile overlay of samidorphan L-malate in Formulations B and C at pH 1.
Figure 2C:
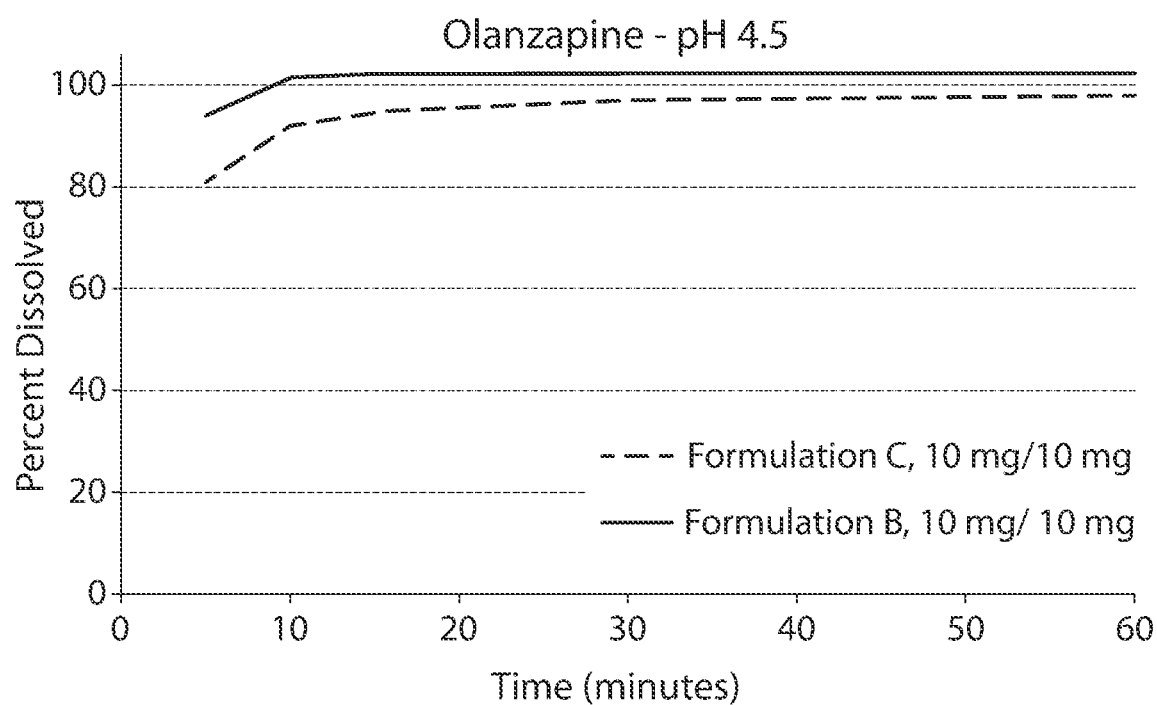
FIG. 2C depicts an exemplary dissolution profile overlay of olanzapine in Formulations B and C at pH 4.5.
Figure 2D:
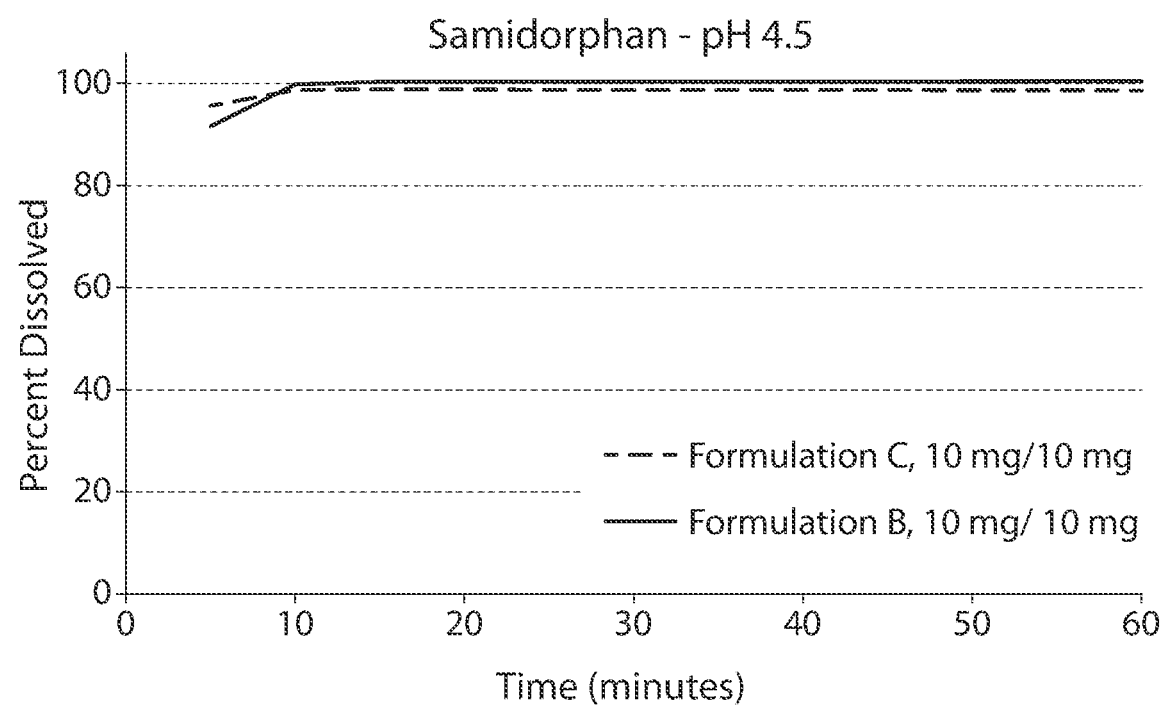
FIG. 2D depicts an exemplary dissolution profile overlay of samidorphan L-malate in Formulations B and C at pH 4.5.
Figure 2E:
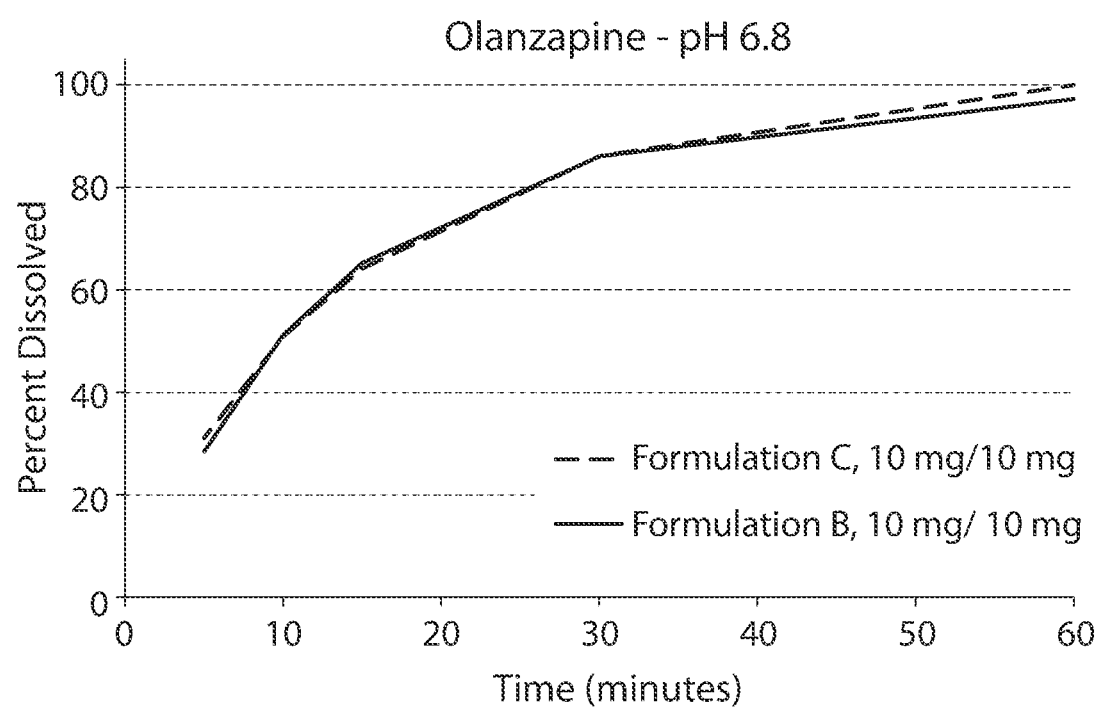
FIG. 2E depicts an exemplary dissolution profile overlay of olanzapine in Formulations B and C at pH 6.8.
Figure 2F:
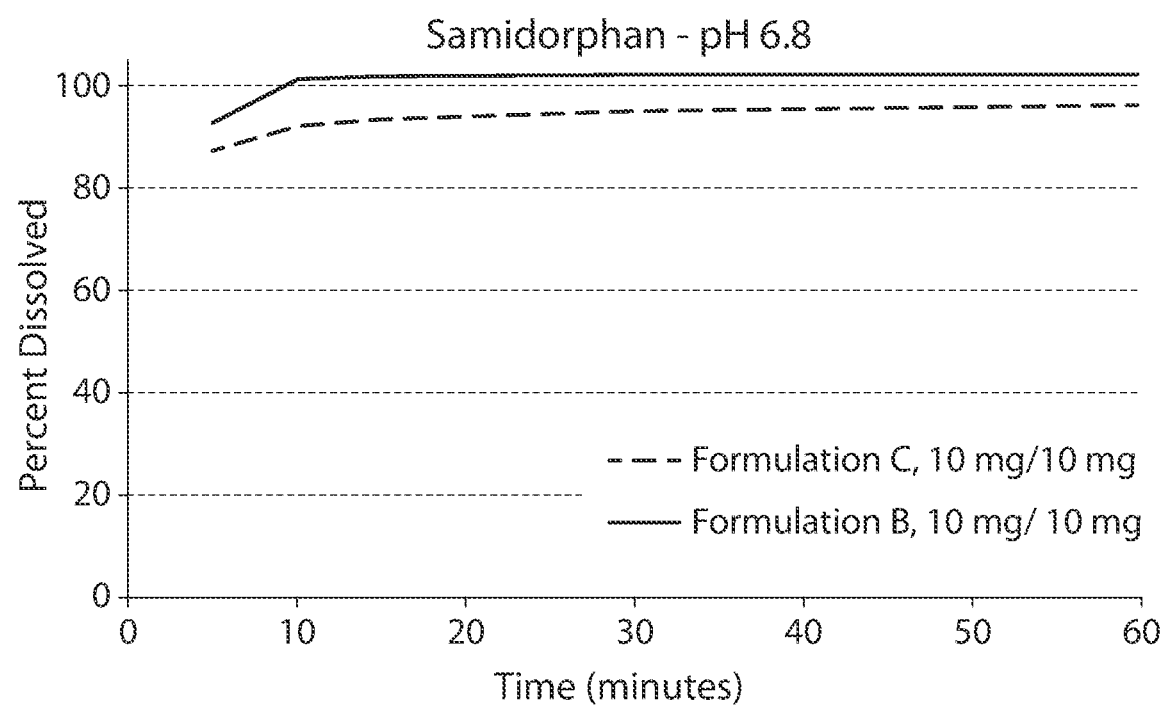
FIG. 2F depicts an exemplary dissolution profile overlay of samidorphan L-malate in Formulations B and C at pH 6.8.

The features and other details of the disclosure will now be more particularly described. Before further description of the present disclosure, certain terms employed in the specification, examples and appended claims are collected here. These definitions should be read in light of the remainder of the disclosure and as understood by a person of skill in the art. Unless defined otherwise, all technical and scientific terms used herein have the same meaning as commonly understood by a person of ordinary skill in the art.

Definitions

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±10%, including±5%, ±1%, and ±0.1% from the specified value, as such variations are appropriate to perform the disclosed methods.

"Individual," "patient," or "subject" are used interchangeably herein and include any animal, including mammals, including mice, rats, other rodents, rabbits, dogs, cats, swine, cattle, sheep, horses, or primates, and humans. The compounds described herein can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods described herein is desirably a mammal in which treatment of a disorder described herein is desired, such as a human.

As used herein, "pharmaceutically acceptable" includes molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable salt(s)" as used herein refers to salts of acidic or basic groups that may be present in compounds used in the compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including, but not limited to, malate (e.g., L-malate), oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts.

As used herein, "treating" includes any effect, e.g., lessening, reducing, modulating, or eliminating, that results in the improvement of the condition, disease, disorder and the like.

As used herein, "wt %" means weight percent.

Tablets

This disclosure in part provides for a pharmaceutically acceptable coated immediate release bilayer tablet for orally delivering olanzapine and samidorphan (e.g., 5 mg, 10 mg, 15 mg, 20 mg), together as a fixed dose, comprising: a first tablet layer having samidorphan or pharmaceutically acceptable salt thereof (e.g., 10 mg samidorphan, or a pharmaceutically acceptable salt of samidorphan in an amount to deliver 10 mg samidorphan); and a second tablet layer having olanzapine (e.g., 2.5 mg, 5 mg, 10 mg, 15 mg or 20 mg of olanzapine), and a film coating; wherein the tablet releases at least 85% of both the olazanpine and the samidorphan after 15 minutes when the tablet is tested in 500 mL 0.1N hydrochloric acid at pH 1.0 using a USP Apparatus II (Paddle Method) at 37° C., with a paddle speed of 75 rpm and using a three-prong sinker. Such contemplated tablets may have less than or about 0.1% wt % to about 1.0 wt %, e.g., about 0.5 wt % or less of impurities due to olanzapine or samidorphan degradation as detected by HPLC, at 6 months, 9 months and/or 12 months or more of storage in a closed container (e.g., a container at 25° C. and 60% relative humidity and optionally containing silica gel desiccant.) Such contemplated tablets may further comprise pharmaceutically acceptable excipients such as: diluents, glidants, disintegrants and lubricants, which may be present separately in any layer or layers of the multi-layer tablets.

For example, a first tablet layer may further comprise: about 75-90 wt % of a first diluent, based on the weight of the first tablet layer; a first glidant; a first disintegrant; and a first lubricant. In some embodiments, a second tablet layer further comprises: about 75-90 wt % of a second diluent; based on the weight of the second tablet layer; a second glidant; a second disintegrant; and a second lubricant. The first and second diluent may be the same or may be different, and for example, the first and second diluent may each independently selected from the group consisting of lactose or a hydrate thereof, microcrystalline cellulose, mannitol, sorbitol, xylitol, dicalcium phosphate, starch, and combinations thereof.

The first and second lubricant may be for example, each independently selected from the group consisting of a pharmaceutically acceptable salt of a stearate, stearic acid, or a combination thereof, and the first and second disintegrant may each independently selected from the group consisting of polyvinylpyrrolidone (crospovidone), crosslinked sodium carboxymethyl cellulose (croscarmellose sodium), sodium starch glycolate and combinations thereof. The first and second glidant may be, for example, each independently selected from the group consisting of silicon dioxide, talc, a carbonate salt and combinations thereof.

Contemplated pharmaceutically acceptable coated immediate release bilayer tablets can include 2.5 mg olanzapine, 5 mg olanzapine, 10 mg olanzapine, or 15 mg olanzapine. In some embodiments, the pharmaceutically acceptable coated immediate release bilayer tablet comprises 20 mg olanzapine. For example, a second tablet layer may have 5 mg, 10 mg, 15 mg or 20 mg olanzapine.

Provided herein, for example, is a pharmaceutically acceptable coated immediate release bilayer tablet for orally delivering olanzapine and samdorphan as a fixed dose, for example, a tablet that can provide to a patient 10 mg samidorphan and 2.5 mg olanzapine, or provide to a patient 10 mg samidorphan and 5 mg olanzapine, 10 mg samidorphan and 10 mg olanzapine, 10 mg samidorphan and 15 mg olanzapine, or 10 mg samidorphan and 20 mg olanzapine. For example, provided here is a fixed dose tablet comprising: a first tablet layer comprising: 10 mg samidorphan, or a pharmaceutically acceptable salt of samidorphan in an amount to deliver 10 mg samidorphan; about 35-43 wt % microcrystalline cellulose, based on the weight of the first tablet layer; about 37-43 wt % lactose or a hydrate thereof, based on the weight of the first tablet layer; and about 1.5 to about 2 wt % magnesium stearate; a second tablet layer comprising: a dose of olanzapine selected from the group consisting of 5 mg, 10 mg, 15 mg and 20 mg of the olanzapine; about 38-42 wt % microcrystalline cellulose, based on the weight of the second tablet layer; about 46-49 wt % lactose or a hydrate thereof, based on the weight of the second tablet layer; and about 1.0 wt % magnesium stearate; and a film coating over the first and second tablet layer.

In another embodiment, described herein is a pharmaceutically acceptable coated immediate release bilayer tablet for orally delivering 5 mg, 10 mg, 15 mg or 20 mg olanzapine, together with 10 mg of samidorphan as a fixed dose, comprising: a first tablet layer comprising: 13.6 mg samidorphan L-malate; about 40 wt % microcrystalline cellulose, based on the weight of the first tablet layer; about 42 wt % lactose monohydrate, based on the weight of the first tablet layer; and about 1.75 wt % magnesium stearate; a second tablet layer comprising: a dose of olanzapine selected from the group consisting of 5 mg, 10 mg, 15 mg and 20 mg of the olanzapine; about 40 wt % microcrystalline cellulose, based on the weight of the second tablet layer; about 47 wt % lactose or a hydrate thereof, based on the weight of the second tablet layer; and about 1.0 wt % magnesium stearate; and a film coating over the first and second tablet layer.

In another embodiment, described herein is a pharmaceutically acceptable coated immediate release bilayer tablet for orally delivering olanzapine and about 10 mg of samidorphan as a fixed dose, comprising: a first tablet layer comprising: about 10 mg samidorphan or a pharmaceutically acceptable salt of samidorphan in an amount to deliver about 10 mg samidorphan; about 30-45 wt % microcrystalline cellulose, based on the weight of the first tablet layer; about 35-50 wt % lactose or a hydrate thereof, based on the weight of the first tablet layer; and about 0.5 to about 2 wt % magnesium stearate; a second tablet layer comprising: a dose of olanzapine of between 2.5 mg and about 20 mg; about 35-45 wt % microcrystalline cellulose, based on the weight of the second tablet layer; about 45-55 wt % lactose or a hydrate thereof, based on the weight of the second tablet layer; and about 1.0 wt % magnesium stearate; and a film coating over the first and second tablet layer.

The particle size distribution of the samidorphan or samidorphan pharmaceutically acceptable salt (e.g., L-malate) present in a disclosed tablet (e.g., as part of a first tablet layer) may be for example, a (D10) of between about 10 μm to about 80 μm, a (D50) of between about 40 μm to about 200 μm and a (D90) of between about 100 μm to about 300 μm, more preferably a D10 of between about 25 μm and about 50 μm; the D50 of between about 60 μm and about 100 μm. In some embodiments, D90 of the samidorphan (e.g., L-malate salt) is between about 120 μm and about 175 μm. The particle size distribution of the olanzapine may include, for example a (D10) of between 10 μm and 100 μm, a D(50) of between 50 μm and 150 μm and a D(90) of between 150 μm and 300 μm, most preferably a D(10) of not less than 22 μm, a D(50) of between 70 μm and 135 μm, and D(90) of not more than 284 μm. Particle size (diameter) may be determined by conventional techniques such as dynamic light scattering. The 'Dx' nomenclature means that 'x' percent of the particles have a number average diameter ('D') less than or equal to the reported value when measured by static or dynamic light scattering techniques known to those skilled in the art. (e.g. D10=175 μm, means that 10% of particles have a number average diameter of less than or equal to 175 μm), a D50 (or Dv50) of less than 300 μm, means that 50% of the particle population has a diameter of less than or equal to 300 μm. The term "Dx" as used herein refers to a volume based size and is equivalent to the term "DvX" commonly used to characterize particle sizes. Since the particles of the present invention may be irregular in shape, an approximation of the particle size is made on the basis of the volume-based particle size, which specifies the diameter of the sphere that has same volume as a given particle. Unless otherwise specified, all particle sizes are specified in terms of volume-based measurements and are measured by laser light scattering/diffraction. Particle sizes are then determined based on Mie scattering theory.

A disclosed exemplary tablet, in an embodiment, releases at least 85% of olanzapine and at least 85% of the samidorphan after 15 minutes when the tablet is tested in 500 mL USP acetate buffer at pH 4.5 using a USP Apparatus II (Paddle Method) at 37° C., with a paddle speed of 75 rpm and using a three-prong sinker. In some embodiments, a disclosed tablet releases at least 97% of olanzapine and at least 97% of the samidorphan after 30 minutes when the tablet is tested in 500 mL USP acetate buffer at pH 4.5 using a USP Apparatus II (Paddle Method) at 37° C., with a paddle speed of 75 rpm.

Minimal impurities in a disclosed tablet may be present, for example, less than 0.1 wt % impurities, less than 0.5 wt % impurities, e.g., less than 1.0 wt % impurities, from olanzapine degradation, are detected, using HPLC, after the tablet is stored for 3 months, 6 months, or e.g., 9 months, in a closed container containing 250 g silica gel desiccant at 25° C. and 60% relative humidity. In some embodiments, the tablet has 0.5 wt % or fewer impurities (or e.g., 1.0 wt % or less impurities) due to the olanzapine or the samidorphan degradation as detected by HPLC, at 6 months of storage in a blister pack at 25° C. and 60% relative humidity.

An exemplary first tablet layer may further comprise about 2.0 wt % crospovidone, and/or about 0.5 wt % silicon dioxide. and/or. In some embodiments, the second tablet layer may include about 1.0 wt % crospovidone and/or 0.5 wt % silicon dioxide Contemplated film coatings for the disclosed tablets may include an Opadry II 33K film coat. In some embodiments, the pharmaceutically acceptable coated immediate release bilayer tablet comprises 2.5 mg olanzapine. In some embodiments, the pharmaceutically acceptable coated immediate release bilayer tablet comprises 5 mg olanzapine. In some embodiments, the pharmaceutically acceptable coated immediate release bilayer tablet comprises 10 mg olanzapine. In some embodiments, the pharmaceutically acceptable coated immediate release bilayer tablet comprises 15 mg olanzapine. In some embodiments, the pharmaceutically acceptable coated immediate release bilayer tablet comprises 20 mg olanzapine.

In a preferred embodiment, described herein is a pharmaceutically acceptable coated immediate release bilayer tablet for orally delivering olanzapine and 10 mg of samidorphan together as a fixed dose, comprising: a first tablet layer having 10 mg samidorphan, or a pharmaceutically acceptable salt of samidorphan in an amount to deliver 10 mg samidorphan; and a second tablet layer having 2.5 mg, 5 mg, 10 mg, 15 mg or 20 mg of olanzapine, and a film coating; wherein the tablet releases at least 80% of both the olazanpine and the samidorphan after 15 minutes when the tablet is tested in 500 mL USP acetate buffer at pH 4.5 using a USP Apparatus II (Paddle Method) at 37° C., with a paddle speed of 75 rpm and using a three-prong sinker.

In another preferred embodiment, a pharmaceutically acceptable coated immediate release bilayer tablet for orally delivering olanzapine and 10 mg or 20 mg of samidorphan as a fixed dose, comprises: a first tablet layer comprising: 10 mg or 20 mg samidorphan or a pharmaceutically acceptable salt of samidorphan in an amount to deliver 10 mg or 20 mg samidorphan; about 30-50 wt % microcrystalline cellulose, based on the weight of the first tablet layer; about 35-50 wt % lactose or a hydrate thereof, based on the weight of the first tablet layer; optionally about 3.0 to about 7.0 wt % crospovidone; optionally about 0.5 to about 1.5 wt % colloidal silica; and about 1.5 to about 2.5 wt % magnesium stearate; a second tablet layer comprising: a dose of olanzapine selected from the group consisting of 2.5 mg, 5 mg, 10 mg, 15 mg and 20 mg of the olanzapine; about 30-50 wt % microcrystalline cellulose, based on the weight of the second tablet layer; about 35-50 wt % lactose monohydrate, based on the weight of the second tablet layer; optionally about 3.0 to about 7.0 wt % crospovidone; optionally about 0.5 to about 1.5 wt % colloidal silica; and about 0.5 to about 1.25 wt % magnesium stearate; and a film coating over the first and second tablet layer.

Also contemplated by this disclosure is a pharmaceutically acceptable coated immediate release bilayer tablet for orally delivering 5 mg olanzapine and 10 mg of samidorphan as a fixed dose, comprising: 5 mg olanzapine; 13.62 mg samidorphan L-malate; 60 mg microcrystalline cellulose; 65.88 mg lactose monohydrate; 2.5 mg crospovidone; 0.75 mg colloidal silicon dioxide; 2.25 mg magnesium stearate; and a film coating.

In one embodiment, described herein is a pharmaceutically acceptable coated immediate release bilayer tablet for orally delivering 10 mg olanzapine and 10 mg of samidorphan as a fixed dose, comprising: 10 mg olanzapine; 13.62 mg samidorphan L-malate; 80 mg microcrystalline cellulose; 89.63 mg lactose monohydrate; 3.0 mg crospovidone; 1.0 mg colloidal silicon dioxide; 2.75 mg magnesium stearate; and a film coating.

A pharmaceutically acceptable coated immediate release bilayer tablet for orally delivering 15 mg olanzapine and 10 mg of samidorphan as a fixed dose, comprising: 15 mg olanzapine; 13.62 mg samidorphan L-malate; 100 mg microcrystalline cellulose; 113.38 mg lactose monohydrate; 3.5 mg crospovidone; 1.25 mg colloidal silicon dioxide; 3.25 mg magnesium stearate; and a film coating is also contemplated.

Described herein in part is a pharmaceutically acceptable coated immediate release bilayer tablet for orally delivering 20 mg olanzapine and 10 mg of samidorphan as a fixed dose, comprising: 20 mg olanzapine; 13.62 mg samidorphan L-malate; 120 mg microcrystalline cellulose; 137.13 mg lactose monohydrate; 4.0 mg crospovidone; 1.5 mg colloidal silicon dioxide; 3.75 mg magnesium stearate; and a film coating.

Further described herein is a pharmaceutically acceptable coated immediate release bilayer tablet for orally delivering olanzapine and 20 mg of samidorphan as a fixed dose, comprising: a first tablet layer comprising: 20 mg samidorphan or a pharmaceutically acceptable salt of samidorphan in an amount to deliver 20 mg samidorphan; about 35-43 wt % microcrystalline cellulose, based on the weight of the first tablet layer; about 37-43 wt % lactose or a hydrate thereof, based on the weight of the first tablet layer; and about 0.5 to about 2 wt % magnesium stearate; a second tablet layer comprising: a dose of olanzapine selected from the group consisting of 2.5 mg, 5 mg, 10 mg, 15 mg and 20 mg of the olanzapine; about 38-42 wt % microcrystalline cellulose, based on the weight of the second tablet layer; about 46-49 wt % lactose or a hydrate thereof, based on the weight of the second tablet layer; and about 0.5 to about 1.5 wt % magnesium stearate; and a film coating over the first and second tablet layer.

A pharmaceutically acceptable coated immediate release bilayer tablet for orally delivering olanzapine and 10 mg of samidorphan as a fixed dose is also provided, comprising: a first tablet layer comprising: 10 mg samidorphan or a pharmaceutically acceptable salt of samidorphan in an amount to deliver 10 mg samidorphan; about 35-43 wt % microcrystalline cellulose, based on the weight of the first tablet layer; about 37-43 wt % lactose or a hydrate thereof, based on the weight of the first tablet layer; and about 1.5 to about 2 wt % magnesium stearate; a second tablet layer comprising: a dose of olanzapine selected from the group consisting of 5 mg, 10 mg, 15 mg and 20 mg of the olanzapine; about 38-42 wt % microcrystalline cellulose, based on the weight of the second tablet layer; about 46-49 wt % lactose or a hydrate thereof, based on the weight of the second tablet layer; and about 1.0 wt % magnesium stearate; and a film coating over the first and second tablet layer; wherein the tablet releases at least 85% of olazanpine and at least 85% of the samidorphan after 15 minutes when the tablet is tested in 500 mL USP acetate buffer at pH 4.5 using a USP Apparatus II (Paddle Method) at 37° C., with a paddle speed of 75 rpm and using a three-prong sinker.

Preferably the bilayer tables are manufactured by compressing separate blends, one containing olanzapine and the other containing samidorphan L-malate, into bilayer tablets. It is most preferable if the same samidorphan and olanzapine blends are used for multiple tablet strengths, with only the olanzapine blend weight being adjusted to achieve the required olanzapine dose in the tablet and the samidorphan blend weight being kept constant. As a result of this formulation approach, it is possible to prepare, for example, a bilayer tablet for delivering 5 mg of olanzapine and 10 mg of samidorphan (5/10), 10 mg of olanzapine and 10 mg of samidorphan (10/10), 15 mg of olanzapine and 10 mg of samidorphan (15/10) and 20 mg of olanzapine and 10 mg of samidorphan (20/10) dose strengths. The advantage that this formulation approach offers is that it allows the same olanzapine and samidorphan blends to be used to create different olanzapine strength compositions, without the need to adjust the components or their respective quantities of the olanzapine blend layer.

Methods of Treatment

Also contemplated herein is a method of treating a patient suffering from a mental illness, comprising administering to the patient a therapeutically effective amount of olanzapine and samidorphan as one or more tablets described herein (e.g., an immediate release bilayer tablet described herein). Contemplated mental illness may be selected from the group consisting of schizophreniform disorder, schizoaffective disorder, severe schizoaffective disorder with psychotic features, bipolar I disorders with a single manic episode, severe bipolar I disorders with psychotic features, bipolar I disorders manifesting a mixed most recent episode, severe bipolar I disorders with psychotic features, brief psychotic disorders, psychotic disorders NOS, paranoid personality disorders, schizoid personality disorders, schizophrenia, schizotypal personality disorders with sedative, hypnotic, or anxiolytic manifestations, major depressive disorders with psychotic features, dementia, acute mania, psychotic agitation, unipolar disorder, and psychotic disorders due to specific general medical conditions. In some embodiments, the tablet is orally administered to the patient.

In some embodiments, the mental illness is a selected from the group consisting of schizophreniform disorder, schizoaffective disorder, severe schizoaffective disorder with psychotic features, bipolar I disorders with a single manic episode, severe bipolar I disorders with psychotic features, bipolar I disorders manifesting a mixed most recent episode, severe bipolar I disorders with psychotic features, brief psychotic disorders, psychotic disorders NOS, paranoid personality disorders, schizoid personality disorders, schizophrenia, schizotypal personality disorders with sedative, hypnotic, or anxiolytic manifestations, major depressive disorders with psychotic features, dementia, acute mania, psychotic agitation, unipolar disorder, and psychotic disorders due to specific general medical conditions.

For example, provided herein is a method of treating schizophrenia or bipolar disorder I, e.g., in adults and/or children in need thereof, comprising administering to the adult or child once daily a disclosed tablet, for example, a disclosed tablet having 10 mg samidorphan and 5 mg, 10 mg, 15 mg or 20 mg olanzapine.

Also provided herein is a method of treating bipolar disorder I, e.g., in adults and/or children in need thereof, comprising administering to the adult or child once daily a disclosed tablet, for example, a disclosed tablet having 10 mg samidorphan and 5 mg, 10 mg, 15 mg or 20 mg olanzapine. For example, provided herein is a method of acutely treating manic and mixed episodes of bipolar disorder I, or a method of maintaining monotherapy treatment in a patient suffering from bipolar disorder I, comprising administering to the adult or child once daily a disclosed tablet, for example, a disclosed tablet having 10 mg samidorphan and 2.5 mg, 5 mg, 10 mg, 15 mg or 20 mg olanzapine.

Provided herein, in another embodiment, is a method of manic or mixed episodes of bipolar disorder I, e.g., in an adult patient and/or pediatric patient in need thereof, wherein the patient is also administered an adjunct treatment of valproate or lithium, comprising administering to the patient once daily a disclosed tablet, for example, a disclosed tablet having 10 mg samidorphan and 2.5 mg, 5 mg, 10 mg, 15 mg or 20 mg olanzapine.

Kits

Also provided herein are kits for use, (e.g., for use in the methods of treatment described herein), comprising a tablet described herein (e.g., an immediate release bilayer tablet described herein). Such kits include a suitable dosage form such as those described above and instructions describing the method of using such dosage form to mediate, reduce or prevent inflammation. The instructions would direct the consumer or medical personnel to administer the dosage form according to administration modes known to those skilled in the art. Such kits could advantageously be packaged and sold in single or multiple kit units. An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets to be packed. Next, the tablets are placed in the recesses and the sheet of relatively stiff material is sealed against the plastic foil at the face of the foil which is opposite from the direction in which the recesses were formed. As a result, the tablets are sealed in the recesses between the plastic foil and the sheet. Preferably the strength of the sheet is such that the tablets can be removed from the blister pack by manually applying pressure on the recesses whereby an opening is formed in the sheet at the place of the recess. The tablet can then be removed via said opening.

EXAMPLES

Abbreviations: SAM: samidorphan; OLZ: olanzapine; RH: relative humidity; HPLC: high performance liquid chromatography; rpm: revolutions per minute; USP: United States Pharmacopeia; LOQ: limit of quantification.

Example 1. Incompatibility of Olanzapine and Samidorphan

The chemical compatibility between olanzapine form I and samidorphan L-malate was determined by grinding the two drug substances together with a mortar and pestle and placing then on stability at 40° C./75% RH in open and closed vial configurations. Chemical incompatibility was observed between olanzapine and samidorphan L-malate. as olanzapine is susceptible to increased degradation in the presence of samidorphan L-malate, which is further increased with higher exposure to humidity.

Samples in 20 ml Wheaton scintillation vials were stored at 40° C./75% RH in open and closed vial configurations. Closed vials were vials closed with a urea cap and wrapped using parafilm under ambient conditions. The contents of the vials were tested at the start of the study and after 2, 6 and 12 weeks. At each time point samples were analysed by reversed phase HPLC (Waters ACQUITY UPLC H-Class System) with ACQUITY PDA Detector using a Waters ACQUITY UPLC CSH C18 Column, 3 mm×100 mm, and a gradient elution of acetate buffer pH 5.1 and 50/50 (v/v) acetonitrile/methanol. Detection of olanzapine was performed at 260 nm and samidorphan at 305 nm. The olanzapine/samidorphan mix samples were analyzed in duplicate and the average results were reported. The results for the olanzapine and samidorphan L-malate chemical stability are reported as percent total impurities in Table 1. Olanzapine related compound B was the major impurity observed and percent level is reported in Table 2.

TABLE 1

Percentage Total Impurities of Olanzapine and Samidorphan at 40° C./75 RH

| SAM-PLE | INI-TIAL | OPEN | | | CLOSED | | |
|---|---|---|---|---|---|---|---|
| | | 2 WEEK | 6 WEEK | 12 WEEK | 2 WEEK | 6 WEEK | 12 WEEK |
| OLZ | 0.00 | 0.00 | 0.00 | 0.00 | 0.00 | 0.00 | 0.00 |
| SAM | 0.00 | 0.00 | 0.00 | 0.00 | 0.00 | 0.00 | 0.00 |
| OLZ + SAM | 0.00 | 0.05 | 0.22 | 0.84 | 0.00 | 0.12 | 0.48 |

TABLE 2

Percentage Related Compound B Impurity 40° C./75% RH

| SAM-PLE | INI-TIAL | OPEN | | | CLOSED | | |
|---|---|---|---|---|---|---|---|
| | | 2 WEEK | 6 WEEK | 12 WEEK | 2 WEEK | 6 WEEK | 12 WEEK |
| OLZ | 0.01 | <LOQ | ND | ND | ND | ND | ND |
| OLZ + SAM | 0.02 | 0.05 | 0.22 | 0.79 | <LOQ | 0.12 | 0.33 |

ND: ≤LOD (0.02 wt %),
LOQ: 0.05 wt %

Results from the chemical compatibility analysis by HPLC show that there was no significant level of any related impurity above the LOQ in either the olanzapine or samidorphan L-malate drug substance, when stored separately. The highest level of related impurities was detected in the drug substance mixture, with olanzapine related compound B as the major degradant detected and no samidorphan related impurities detected. The data therefore shows that olanzapine is susceptible to increased degradation in the presence of samidorphan L-malate thus making them chemically incompatible. The levels for the olanzapine related impurity in the open vial are higher than in the closed vial condition due to the increased hydrolysis of the olanzapine at 40° C./75% RH.

Example 2. Exemplary Manufacturing Process of a Bilayer Tablet for Oral Delivery of Olanzapine and Samidorphan An exemplary manufacturing process for a bilayer tablet for oral delivery of olanzapine and samidorphan using two direct compression blends, one containing olanzapine and the other containing samidorphan L-malate, which are compressed into bilayer tablets, is described below.

Step 1—Dispensing: All materials for manufacturing bilayer tablets are dispensed.

Step 2—Samidorphan-Colloidal Silicon Dioxide Premix: Samidorphan L-malate and colloidal silicon dioxide are charged into a vessel and premixed.

Step 3—Charging and Material Delumping: Materials for an olanzapine blend (olanzapine, microcrystalline cellulose, crospovidone, and silicon dioxide) are charged into an Intermediate Bulk Container (IBC), and materials for the samidorphan L-malate blend (samidorphan L-malate and colloidal silicon dioxide premix, microcrystalline cellulose, lactose monohydrate, and crospovidone) are charged into a separate IBC, in an order to facilitate layering of the drug substance between excipient layers. Separately, each IBC is docked above a rotating impeller screening mill. The screening mill is equipped with a screen with holes 0.045-0.055 inches (1.14 mm to about 1.4 mm) in diameter. The speed is set to achieve the desired material throughput. Independently, the materials are passed through the mill and collected into separate IBCs.

Step 4—Main Blending: Next, for each blend, the IBC is docked to a diffusion bin blender (tumble) and the materials are blended for a defined time at a fixed speed.

Step 5—Lubrication Blending: Next, magnesium stearate is sieved through a 425 micron (40 mesh) hand screen and added to the IBC for each blend. For each blend, the IBC is docked to a diffusion bin blender (tumble) and the blend is lubricated for a defined time at a fixed speed.

Step 6—Compression: Next, lubricated blends are gravity-fed to the tablet press hoppers from both IBCs. A power-assisted rotary tablet press is set up with appropriate tablet tooling, a tablet deduster, and a metal detector. During tablet compression, checks are performed on the first layer tablet weight, bilayer tablet weight, and thickness at defined intervals. Fill depth and compression force are monitored and adjusted to achieve in-process control acceptance criteria. Appropriate control over the aforementioned variables ensures that the desired release characteristics for the tablet are achieved.

Step 7—Coating and Drying: Next, the OPADRY® II aqueous coating suspension is used to apply a cosmetic film coating to the tablets. The coating process is performed in a fully perforated coating pan to achieve the target weight gain. The coated tablets are dried to a specified loss-on-drying (LOD) value. Control of tablet water content is achieved through careful control of the exhaust temperature during coating and the inlet temperature during drying. After coating and drying, samples are removed for quality control release testing of the bulk finished product.

Step 8—Bulk Packaging: Tablets are discharged from the coater into a high-density polyethylene (HDPE) drum lined with two low-density polyethylene (LDPE) bags, with desiccant between the bags, and stored at controlled room temperature.

Step 9: Weight Sorting and Bulk Repackaging: The coated tablets are sorted by weight to remove delaminated and broken tablets. The acceptable tablets are repackaged into a 75L HDPE drum lined with two (2) LDPE bags, with desiccant between the bags, and stored at controlled room temperature.

Step 10: The coated tablets are packaged into bottles. Silica gel desiccant is added to the bottle to control moisture and ensure stability over shelf life. Control of water permeation into the packaging of the product over its shelf life is an essential step to achieve target purity. This is controlled through the use of desiccant and an induction seal on the bottle. Sealing controlled by the hood height, induction sealing power and line speed.

Example 3. Tablet Formulations

Immediate release bilayer tablet formulations of olanzapine and samidorphan L-malate were prepared. Depending on the strength, three discrete variations in formulation (defined as Formulations A through C) have been manufactured. A comparison of compositions for olanzapine and samidorphan L-malate formulation variations by individual tablet strengths is provided in Table 3, Table 4, Table 5, Table 6 and Table 7 respectively. A comparison of the compositions of olanzapine and samidorphan blends for formulation variations is provided in Table 8, Table 9 and Table 10 respectively.

Referring to Formulation A, for example and the various olanzapine strength compositions shown in tables 3-7, bilayer tablets were manufactured by compressing separate blends, one containing olanzapine and the other containing samidorphan L-malate, into bilayer tablets. The same components are used for all tablet strengths, with the olanzapine blend weight adjusted based on tablet strength and the samidorphan blend weight kept constant, resulting in tablets which delivered 10 mg of samidorphan and 2.5 mg, 5 mg, 10 mg, 15 mg and 20 mg of olanzapine respectively. This allowed the same olanzapine and samidorphan blends to be used to create different olanzapine strength compositions.

TABLE 3

2.5 mg Olanzapine/10 mg Samidorphan Tablet Composition

| Component | Amount (mg) per tablet | Amount (% wt) per coated tablet |
|---|---|---|
| Olanzapine | 2.5 | 1.67 |
| Samidorphan L-malate | 13.62 | 9.08 |
| Microcrystalline cellulose, NF | 61.14 | 40.76 |
| Lactose monohydrate, NF | 67.24 | 44.83 |
| Crospovidone, NF | 2.50 | 1.67 |
| Colloidal silicon dioxide, NF | 0.75 | 0.5 |
| Magnesium stearate, NF | 2.25 | 1.5 |
| Total uncoated tablet | 150.00 | 100 |

TABLE 4

5 mg Olanzapine/10 mg Samidorphan Tablet Composition

| Component | Amount (mg) per tablet | Amount (% wt) per coated tablet |
|---|---|---|
|  | Formulation A | |
| Olanzapine | 5.00 | 3.21 |
| Samidorphan L-malate | 13.62 | 8.73 |
| Microcrystalline cellulose, NF | 60.00 | 38.46 |
| Lactose monohydrate, NF | 65.88 | 42.23 |
| Crospovidone, NF | 2.50 | 1.60 |
| Colloidal silicon dioxide, NF | 0.75 | 0.48 |
| Magnesium stearate, NF | 2.25 | 1.44 |
| Total uncoated tablet | 150.00 | — |
| Film coat suspension | | |
| Opadry ® II yellow 33K120005 | 6.00 | 3.85 |
| Total coated tablet | 156.00 | 100.00 |

TABLE 5

10 mg Olanzapine/10 mg Samidorphan Tablet Compositions

| Component | Amount (mg) per tablet Formulation A | Amount (% wt) per coated tablet Formulation A | Amount (mg) per tablet Formulation B | Amount (% wt) per coated tablet Formulation B | Amount (mg) per tablet Formulation C | Amount (% wt) per coated tablet Formulation C |
|---|---|---|---|---|---|---|
| Olanzapine | 10.00 | 4.81 | 10.00 | 4.81 | 9.95 | 4.78 |
| Samidorphan L-malate | 13.62 | 6.55 | 13.62 | 6.55 | 13.55 | 6.51 |
| Microcrystalline cellulose, NF | 80.00 | 38.46 | 80.00 | 38.46 | 79.60 | 38.27 |
| Lactose monohydrate, NF | 89.63 | 43.09 | 90.38 | 43.45 | 89.93 | 43.24 |
| Crospovidone, NF | 3.00 | 1.44 | 3.00 | 1.44 | 2.99 | 1.44 |
| Colloidal silicon dioxide, NF | 1.00 | 0.48 | 1.00 | 0.48 | 1.99 | 0.96 |
| Magnesium stearate, NF | 2.75 | 1.32 | 2.00 | 0.96 | 1.99 | 0.96 |
| Total uncoated tablet | 200.00 | | 200.00 | | 200.00 | |
| Film coat suspension | | | | | | |
| Opadry ® II orange 33K130001 | 8.00 | 3.85 | 8.00 | 3.85 | 8.00 | 3.85 |
| Total coated tablet | 208.00 | 100.00 | 208.00 | 100.00 | 208.00 | 100.00 |

TABLE 6

15 mg Olanzapine/10 mg Samidorphan Tablet Compositions

| Component | Amount (mg) per tablet Formulation A | Amount (% wt) per coated tablet Formulation A | Amount (mg) per tablet Formulation B | Amount (% wt) per coated tablet Formulation B |
|---|---|---|---|---|
| Olanzapine | 15.00 | 5.77 | 15.00 | 5.77 |
| Samidorphan L-malate | 13.62 | 5.24 | 13.62 | 5.24 |
| Microcrystalline cellulose, NF | 100.00 | 38.46 | 100.00 | 38.46 |
| Lactose monohydrate, NF | 113.38 | 43.61 | 114.13 | 43.90 |
| Crospovidone, NF | 3.50 | 1.35 | 3.50 | 1.35 |
| Colloidal silicon dioxide, NF | 1.25 | 0.48 | 1.25 | 0.48 |
| Magnesium stearate, NF | 3.25 | 1.25 | 2.50 | 0.96 |
| Total uncoated tablet | 250.00 | | 250.00 | |
| Film coat suspension | | | | |
| Opadry ® II blue 33K105011 | 10.00 | 3.85 | 10.00 | 3.85 |
| Total coated tablet | 260.00 | 100.00 | 260.00 | 100.00 |

TABLE 7

20 mg Olanzapine/10 mg Samidorphan Tablet Compositions

| Component | Amount (mg) per tablet Formulation A | Amount (% wt) per tablet Formulation A | Amount (mg) per tablet Formulation B | Amount (% wt) per tablet Formulation B |
|---|---|---|---|---|
| Olanzapine | 20.00 | 6.41 | 20.00 | 6.41 |
| Samidorphan L-malate | 13.62 | 4.37 | 13.62 | 4.37 |
| Microcrystalline cellulose, NF | 120.00 | 38.46 | 120.00 | 38.46 |
| Lactose monohydrate, NF | 137.13 | 43.95 | 137.88 | 44.19 |
| Crospovidone, NF | 4.00 | 1.28 | 4.00 | 1.28 |
| Colloidal silicon dioxide, NF | 1.50 | 0.48 | 1.50 | 0.48 |
| Magnesium stearate, NF | 3.75 | 1.20 | 3.00 | 0.96 |
| Total uncoated tablet | 300.00 | | 300.00 | |
| Film coat suspension | | | | |
| Opadry ® II pink 33K140002 | 12.00 | 3.85 | 12.00 | 3.85 |
| Total coated tablet | 312.00 | 100.00 | 312.00 | 100.00 |

TABLE 8

Olanzapine Blend Compositions for tablet layer inclusion

| Component | % wt Formulation A and B | % wt Formulation C |
|---|---|---|
| Olanzapine | 10.00 | 9.95 |
| Microcrystalline cellulose, NF | 40.00 | 39.80 |
| Lactose monohydrate, NF | 47.50 | 47.26 |
| Crospovidone, NF | 1.00 | 1.00 |
| Colloidal silicon dioxide, NF | 0.50 | 1.00 |
| Magnesium stearate, NF | 1.00 | 0.99 |
| Total | 100.0 | 100.00 |

An alternative olanzapine layer blend for a 10 mg samidorphan and 2.5 mg olanzapine bilayer tablet formulation is shown below:

TABLE 9

Alternative Olanzapine Blend Compositions for tablet layer inclusion (2.5 mg Olanzapine strength)

| Component | Amount (mg) per tablet | Amount (% wt) per coated tablet |
|---|---|---|
| Olanzapine | 2.5 | 5.00 |
| Microcrystalline cellulose, NF | 21.14 | 42.28 |
| Lactose monohydrate, NF | 25.11 | 50.22 |
| Crospovidone, NF | 0.50 | 1.00 |
| Colloidal silicon dioxide, NF | 0.25 | 0.5 |
| Magnesium stearate, NF | 0.5 | 1.00 |
| Total uncoated tablet | 50.00 | 100 |

TABLE 10

Samidorphan Blend Compositions

| Component | % wt Formulation A | % wt Formulation B | % wt Formulation C |
|---|---|---|---|
| Samidorphan L-malate | 13.62 | 13.62 | 13.55 |
| Microcrystalline cellulose, NF | 40.00 | 40.00 | 39.80 |
| Lactose monohydrate, NF | 42.13 | 42.88 | 42.67 |
| Crospovidone, NF | 2.00 | 2.00 | 1.99 |
| Colloidal silicon dioxide, NF | 0.50 | 0.50 | 0.99 |
| Magnesium stearate, NF | 1.75 | 1.00 | 1.00 |
| Total | 100.0 | 100.00 | 100.00 |

The same excipients were used in both layers and at similar ratios which minimizes the potential of layer separation due to differences in viscoelastic properties between the layers. Microcrystalline cellulose and lactose monohydrate are used as diluents, crospovidone as a disintegrant, colloidal silicon dioxide as a glidant and magnesium stearate as a lubricant. The HPMC-based Opadry® II, a non-functional film coating, was selected to mask the yellow color of the olanzapine layer and to provide differentiation across product strengths, in addition to tablet size and debossment.

The bilayer tablet composition was optimized to i) minimizing friability, (ii) maximizing the olanzapine layer disintegration to approximate that of the total tablet (i.e., samidorphan layer) and to (iii) maximizing hardness, and compactibility profile $R^2$. The latter criterion was selected to ensure the composition was not subject to over-compression, which could lead to tablet defects such as capping and delamination. Separation of layers after compression, was assessed indirectly via observation of fracture mode during hardness testing and tablet disintegration behavior (i.e., disintegration as two independent layers or a whole tablet). The individual blends required to make each optimal tablet composition were the same for all the tablet strengths. This was not necessarily expected a priori but is advantageous for manufacturing operations. The excipient levels were either similar or the same between olanzapine and samidorphan layers thereby providing similar viscoelastic response on compression and reducing the potential for delamination. A subsequent increase to the amount of crospovidone from 1% to 2% in the SAM blend was made to achieve rapid dissolution of samidorphan and define the initial clinical composition known as Formulations B and C described herein.

During further development of Formulation B, undesirable tablet picking was identified during the evaluation of compaction profiles; picking was observed on the SAM layer punch face resulting in picking of the SAM layer. Subsequent compression studies identified the extent of lubrication as the root cause. A lubrication level optimization DOE was performed to map the formulation and process space for varying levels of magnesium stearate (from 1.00% wt/wt to 2.00% wt/wt) in the samidorphan layer. The study was performed using the 5 mg/10 mg bilayer tablet, as these tablets consistently exhibited the worst tablet picking. Samidorphan blends were evaluated for flowability, and bilayer tablets for picking, friability, hardness, disintegration time, and dissolution. Tablet picking was assessed to determine if the appearance CQA target was met. The results showed that the level of magnesium stearate had a significant effect on tablet picking. Based on the acceptable ranges identified, a level of 1.75% wt./wt. magnesium stearate was selected for the SAM layer to eliminate tablet picking. This change resulted in Formulation A, which did not have an impact on any of the other CQAs.

Example 4. In Vitro Dissolution Testing of Tablets

Dissolution tests of the bilayer tablets were performed. Dissolution was performed over pH 1 to 6.8. Twelve tablets (n=12) were analyzed per drug product lot at each pH condition. The pH values and media used for dissolution testing were pH 1 (0.1N hydrochloric acid), pH 4.5 (USP acetate buffer), and pH 6.8 (USP phosphate buffer). The dissolution method parameters (Table 11) included a paddle speed of 75 revolutions per minute to reduce coning and three-prong sinkers to eliminate sticking of tablets to the dissolution vessel.

TABLE 11

Dissolution Parameter Summary

| Variable | Condition |
|---|---|
| Dissolution Apparatus | USP Apparatus II - (Paddle Method) |
| Medium Volume | 500 mL |
| Media Temperature | 37.0° C. ± 0.5° C. |
| Paddle Speed | 75 rpm |
| Dissolution Media | pH 1, 0.1N hydrochloric acid (release method) |
| | pH 4.5, USP acetate buffer |
| | pH 6.8, USP phosphate buffer |
| Sinker | Three-prong sinker |
| Sampling Time Points | 5, 10, 15, 30, and 60 minutes |
| Detection | Fiber-optic or HPLC |

Dissolution Testing of Formulation A.

Dissolution profile overlays of mean data for both olanzapine and samidorphan L-malate in Formulation A primary and supportive stability lots are provided in FIGS. 1A-1F.

Figure 14:
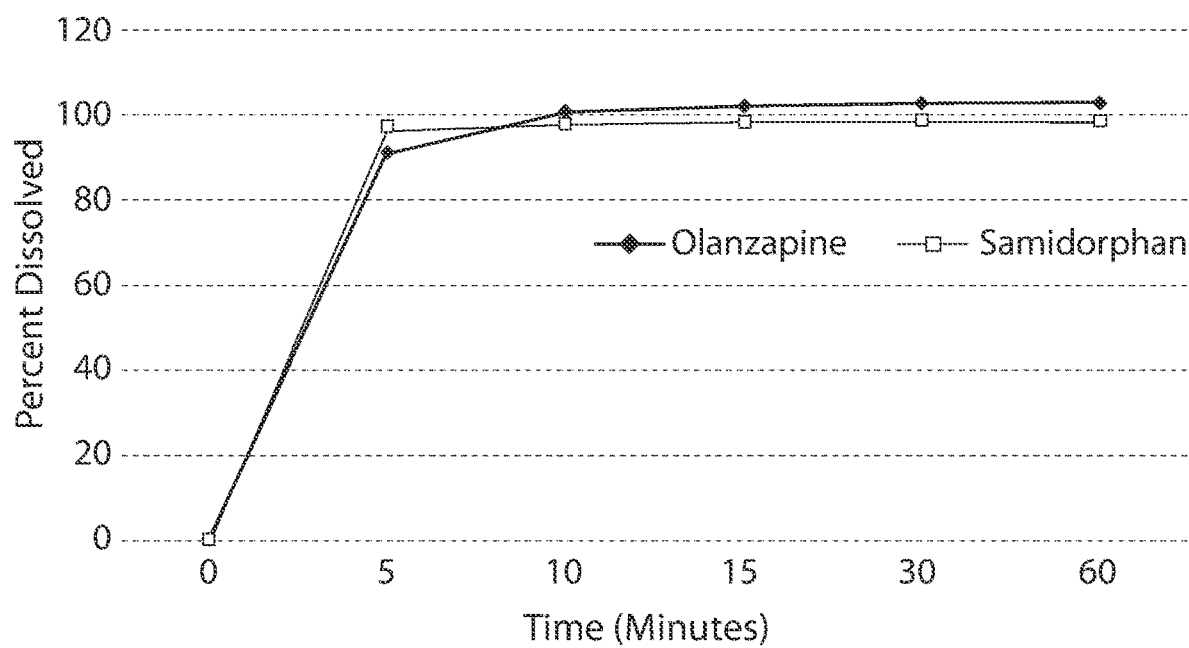
FIG. 14 depicts a dissolution profile overlay of samidorphan L-malate overlaid with the dissolution profile of olanzapine obtained for Formulation A (10/10) at pH 4.5.

An additional dissolution profile overlay of samidorphan L-malate overlaid with the dissolution profile of olanzapine obtained for Formulation A (10/10) at pH 4.5 is provided as FIG. 14.

Comparative Dissolution Testing of Formulations B and C.

Comparable dissolution was demonstrated for the change in CSD between Formulations C and B. Tablets were very rapidly dissolving for olanzapine in pH 1 and 4.5 media. At pH 6.8, olanzapine dissolution slowed due to proximity of the olanzapine pKa values (5.44 and 7.80) to the media pH value, but was similar (f2=85). Tablets were very rapidly dissolving for samidorphan L-malate in all dissolution media. The change in level of CSD did not affect the dissolution of olanzapine and samidorphan L-malate. Dissolution profile overlays of mean data for olanzapine and samidorphan L-malate are provided in FIGS. 2A-2F.

Comparative Dissolution Testing of Formulations B and A.

Figure 3A:
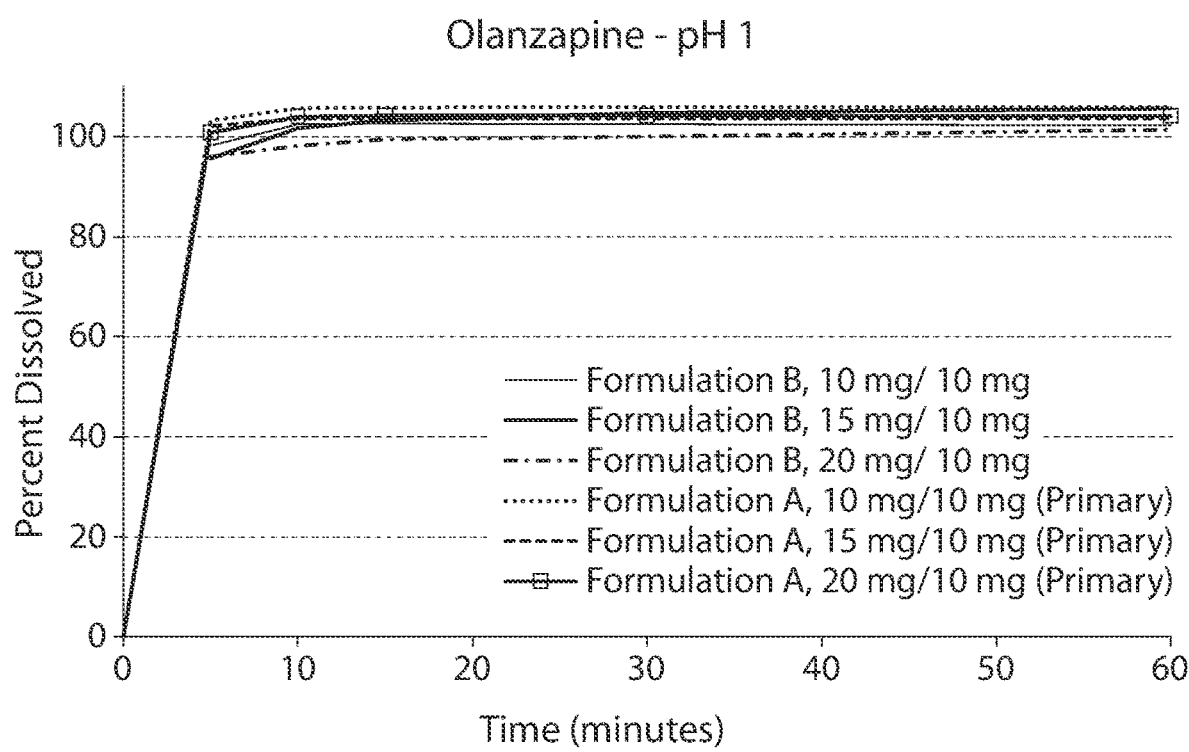
FIG. 3A depicts an exemplary dissolution profile overlay of olanzapine in Formulations B and A at pH 1.
Figure 3B:
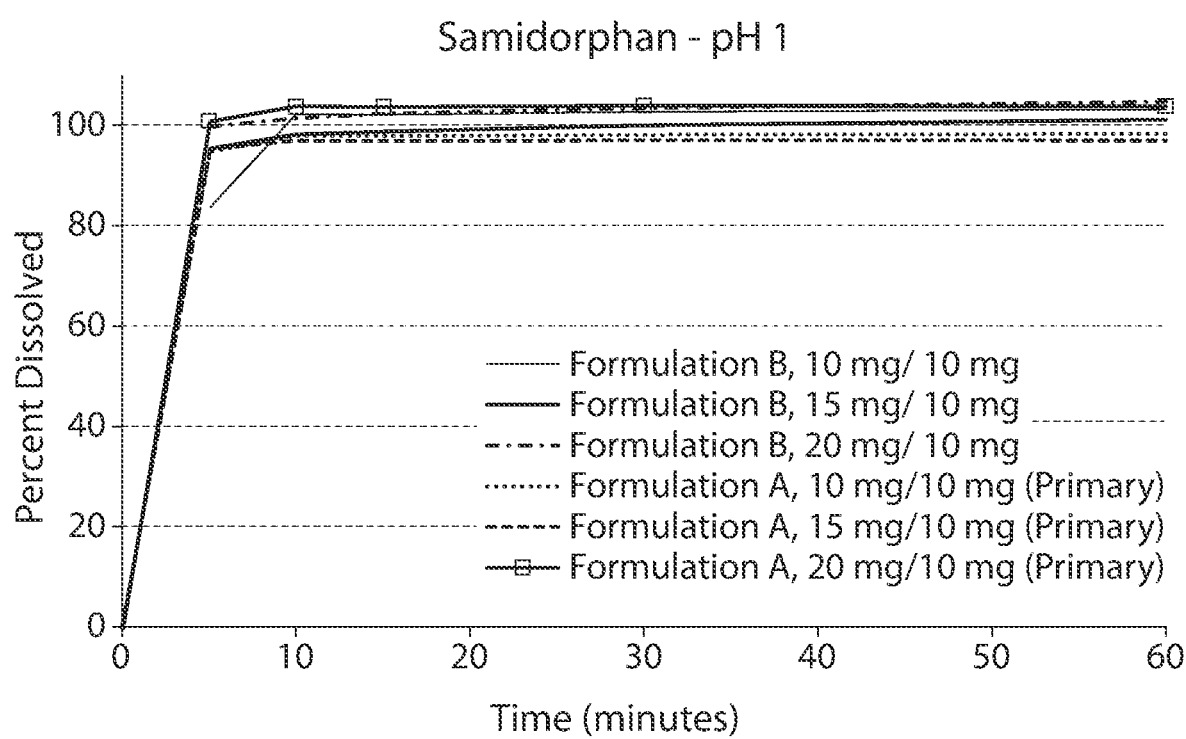
FIG. 3B depicts an exemplary dissolution profile overlay of samidorphan L-malate in Formulations B and A at pH 1.

Comparative dissolution was evaluated using the application release dissolution method to assess the impact of a change in the magnesium stearate between Formulation B and Formulation A. Formulations B and A in the 10 mg/10 mg, 15 mg/10 mg and 20 mg/10 mg tablets had equivalent dissolution profiles in the release method. Tablets were very rapidly dissolving for both olanzapine and samidorphan. The change in level of magnesium stearate did not affect the dissolution of olanzapine or samidorphan L-malate. Dissolution profile overlays of mean data for olanzapine and samidorphan L-malate from a comparative study using the application release method are provided in FIGS. 3A-3B. The Average dissolution values are also depicted below in Tables 12-14. Note that Dissolution percent is based on the dose strength. For a given batch of tablets there is a distribution of drug amount within the tablets around the mean of the dose strength target. Thus the majority of tablets will have the target mean amount (i.e., 10 mg for samidorphan) but some may have a little more and some a little less than the target. Greater than 100% would imply that a particular tablet had slightly more drug than the target dose. Plateau of the curve in each instance however is an indication of complete release.

TABLE 12

Average Dissolution Values - pH 1.0 (0.1N HCl)

| | Percent Dissolved Tablet Formulation | | | | | | | | | | | |
|---|---|---|---|---|---|---|---|---|---|---|---|---|
| | Olanzapine | | | | | | Samidorphan | | | | | |
| Time (Minutes) | 0 | 5 | 10 | 15 | 30 | 60 | 0 | 5 | 10 | 15 | 30 | 60 |
| 5 mg OLZ/10 mg SAM (Primary) | 0 | 105 | 105 | 105 | 105 | 105 | 0 | 98 | 98 | 99 | 98 | 98 |
| 5 mg OLZ/10 mg SAM (Supportive) | 0 | 98 | 103 | 103 | 103 | 103 | 0 | 100 | 100 | 100 | 100 | 101 |
| 10 mg OLZ/10 mg SAM (Primary) | 0 | 103 | 106 | 106 | 106 | 106 | 0 | 95 | 98 | 98 | 98 | 98 |
| 15 mg OLZ/10 mg SAM (Primary) | 0 | 102 | 104 | 104 | 104 | 104 | 0 | 95 | 97 | 97 | 97 | 97 |
| 20 mg OLZ/10 mg SAM (Primary) | 0 | 101 | 104 | 104 | 104 | 104 | 0 | 101 | 104 | 104 | 104 | 104 |
| 20 mg OLZ/10 mg SAM (Supportive) | 0 | 101 | 103 | 103 | 103 | 103 | 0 | 106 | 107 | 107 | 107 | 107 |

TABLE 13

Average Dissolution Values - pH 4.5

| | Percent Dissolved Tablet Formulation | | | | | | | | | | | |
|---|---|---|---|---|---|---|---|---|---|---|---|---|
| | Olanzapine | | | | | | Samidorphan | | | | | |
| Time (Minutes) | 0 | 5 | 10 | 15 | 30 | 60 | 0 | 5 | 10 | 15 | 30 | 60 |
| 5 mg OLZ/10 mg SAM (Primary) | 0 | 94 | 100 | 100 | 100 | 100 | 0 | 99 | 99 | 99 | 99 | 99 |
| 5 mg OLZ/10 mg SAM (Supportive) | 0 | 70 | 92 | 98 | 100 | 100 | 0 | 99 | 100 | 100 | 100 | 100 |
| 10 mg OLZ/10 mg SAM (Primary) | 0 | 91 | 100 | 101 | 102 | 102 | 0 | 96 | 97 | 98 | 98 | 98 |

TABLE 13-continued

Average Dissolution Values - pH 4.5

Percent Dissolved Tablet Formulation

| | Olanzapine | | | | | | Samidorphan | | | | | |
|---|---|---|---|---|---|---|---|---|---|---|---|---|
| Time (Minutes) | 0 | 5 | 10 | 15 | 30 | 60 | 0 | 5 | 10 | 15 | 30 | 60 |
| 15 mg OLZ/10 mg SAM (Primary) | 0 | 91 | 99 | 100 | 100 | 101 | 0 | 97 | 99 | 99 | 99 | 99 |
| 20 mg OLZ/10 mg SAM (Primary) | 0 | 88 | 97 | 99 | 101 | 101 | 0 | 98 | 101 | 101 | 101 | 100 |
| 20 mg OLZ/10 mg SAM (Supportive) | 0 | 88 | 97 | 99 | 100 | 101 | 1 | 102 | 105 | 105 | 105 | 105 |

TABLE 14

Average Dissolution Values - pH 6.8

Percent Dissolved Tablet Formulation

| | Olanzapine | | | | | | Samidorphan | | | | | |
|---|---|---|---|---|---|---|---|---|---|---|---|---|
| Time (Minutes) | 0 | 5 | 10 | 15 | 30 | 60 | 0 | 5 | 10 | 15 | 30 | 60 |
| 5 mg OLZ/10 mg SAM (Primary) | 0 | 20 | 41 | 53 | 72 | 85 | 0 | 91 | 93 | 94 | 94 | 95 |
| 5 mg OLZ/10 mg SAM (Supportive) | 0 | 11 | 27 | 40 | 68 | 86 | 0 | 95 | 95 | 96 | 96 | 97 |
| 10 mg OLZ/10 mg SAM (Primary) | 0 | 19 | 41 | 55 | 78 | 94 | 0 | 95 | 96 | 97 | 97 | 98 |
| 15 mg OLZ/10 mg SAM (Primary) | 0 | 21 | 43 | 57 | 80 | 94 | 0 | 93 | 95 | 94 | 96 | 97 |
| 20 mg OLZ/10 mg SAM (Primary) | 0 | 18 | 41 | 55 | 78 | 93 | 0 | 87 | 98 | 99 | 100 | 101 |
| 20 mg OLZ/10 mg SAM (Supportive) | 0 | 21 | 41 | 55 | 77 | 92 | 0 | 96 | 101 | 101 | 103 | 104 |

Example 5. Samidorphan L-Malate Particle Size Comparability Studies

For samidorphan L-malate, a recrystallization process was implemented providing particle size control during manufacturing to intentionally target a particle size distribution similar to the size of the drug product filler excipients. Unmilled and recrystallized grades of samidorphan L-malate were characterized for particle size distribution using 3 unique lots of each. The particle size of unmilled (Primary) and recrystallized samidorphan L-malate (Supportive) batches are presented in Table 15. The recrystallization was targeted to produce material with less fine particles thus increasing the D10. A slight increase in the D50 and decrease in the D90 adjusted the centerpoint of the distribution and decreased the overall span of the distribution. Overall the recrystallized materials had tighter distributions and reduced lot to lot variability, indicating better control. No change in the solid state form was observed between unmilled and recrystallized samidorphan L-malate as assessed by PXRD spectral comparison.

TABLE 15

Particle Size for Unmilled and Recrystallized Samidorphan L-Malate.

| Unmilled | | | | Recrystallized | | | |
|---|---|---|---|---|---|---|---|
| Sample number (particle size measurement) | Particle size (μm) | | | Sample number (particle size measurement) | Particle size (μm) | | |
| | $D_{10}$ | $D_{50}$ | $D_{90}$ | | $D_{10}$ | $D_{50}$ | $D_{90}$ |
| 1 | 8 | 37 | 223 | 4 | 33 | 73 | 130 |
| 2 | 10 | 36 | 231 | 5 | 46 | 90 | 160 |
| 3 | 6 | 28 | 243 | 6 | 42 | 90 | 165 |

Example 6. Stability Studies of Bilayer Tablets

The tablets are manufactured according to the manufacturing process of Example 2. Eight primary batches were manufactured. Seven of these were placed on primary stability, three 5 mg/10 mg OLZ/SAM batches, one 10 mg/10 mg OLZ/SAM batch, and three 20 mg/10 mg OLZ/SAM batches. Two supportive batches, one 5 mg/10 mg OLZ/SAM and one 20 mg/10 mg OLZ/SAM, were also manufactured. Three packaging configurations were employed for stability analysis, 5-count in a 30 cc HDPE induction-sealed bottle with desiccant, and 30-count and 100-count into 60 cc HDPE induction-sealed bottles with desiccant. Table 16 summarizes the package batches used in the primary stability studies.

The statistical analysis of all long-term stability data was performed according to the approach detailed in ICH Q1E. Regression analysis was utilized to evaluate the stability data for the quantitative attributes and establish an expiry period. Expiry period for each attribute was performed by determining the earliest time at which the 95% confidence limit for the mean intersects the proposed acceptance criteria. For acceptance criteria with an upper limit, the upper one-sided 95% confidence limit was compared to the acceptance criteria. For acceptance criteria with a lower limit, the lower one-sided 95% confidence limit was compared to the acceptance criteria. For acceptance criteria with upper and lower limits, the two-sided 95% confidence limit was compared to the acceptance criteria. Each test is conducted using a significance level of 0.05.

SLIMStat® Version 5.0.0 software was used to determine poolability among sample batches across test attributes and to estimate the product expiry period. SLIMStat uses four models to estimate expiry period three of which were required for this analysis: Model 2: Common slope but different intercept; expiration period will be considered the minimum of the expiration period of individual studies;

Model 4: Different intercept and different slope; expiration period for individual batches are estimated by using individual intercepts and individual slopes and the pooled mean square error calculated from all batches.

TABLE 16

Samples in Exemplary Primary Stability Studies.

| Dosage Strength (OLZ/SAM) | Sample Number | Configuration |
|---|---|---|
| 5 mg/10 mg | 1 | 5-count, 30 cc |
| | 2 | HDPE bottle, 1 g |
| | 3 | desiccant canister |
| | 12 | 100-count, 60 cc |
| | 13 | HDPE bottle, 2 g |
| | 14 | desiccant canister |
| 10 mg/10 mg | 4 | 5-count, 30 cc HDPE bottle, 1 g desiccant canister |
| | 8 | 100-count, 60 cc HDPE bottle, 2 g desiccant canister |
| 20 mg/10 mg | 5 | 5-count, 30 cc |
| | 6 | HDPE bottle, 1 g |
| | 7 | desiccant canister |
| | 9 | 100-count, 60 cc |
| | 10 | HDPE bottle, 2 g |
| | 11 | desiccant canister |

For a given test attribute across multiple batches in Table 16, the shortest expiry period was reported based on the regression analysis model (Model 2 or 4 as described above) referenced for that test attribute as detailed in Table 17.

TABLE 17

Expiry Period Determination.

Figure 4:
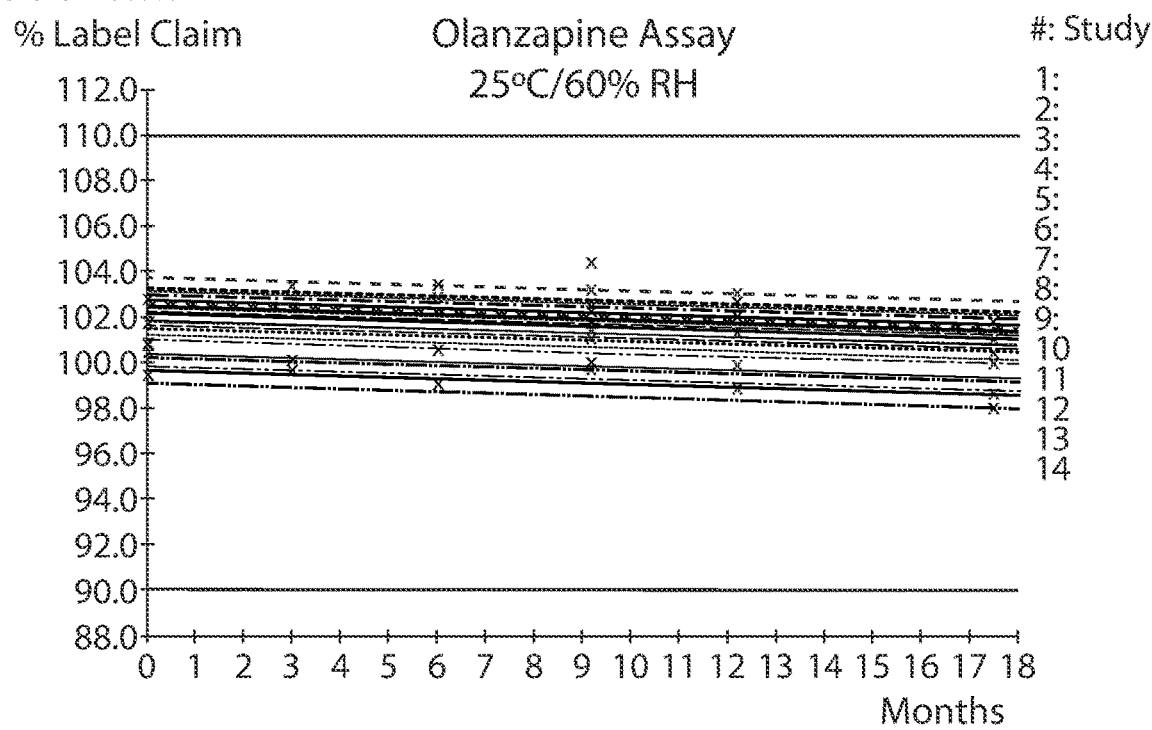
FIG. 4 depicts exemplary shelf life studies of olanzapine in disclosed tablets.
Figure 5:
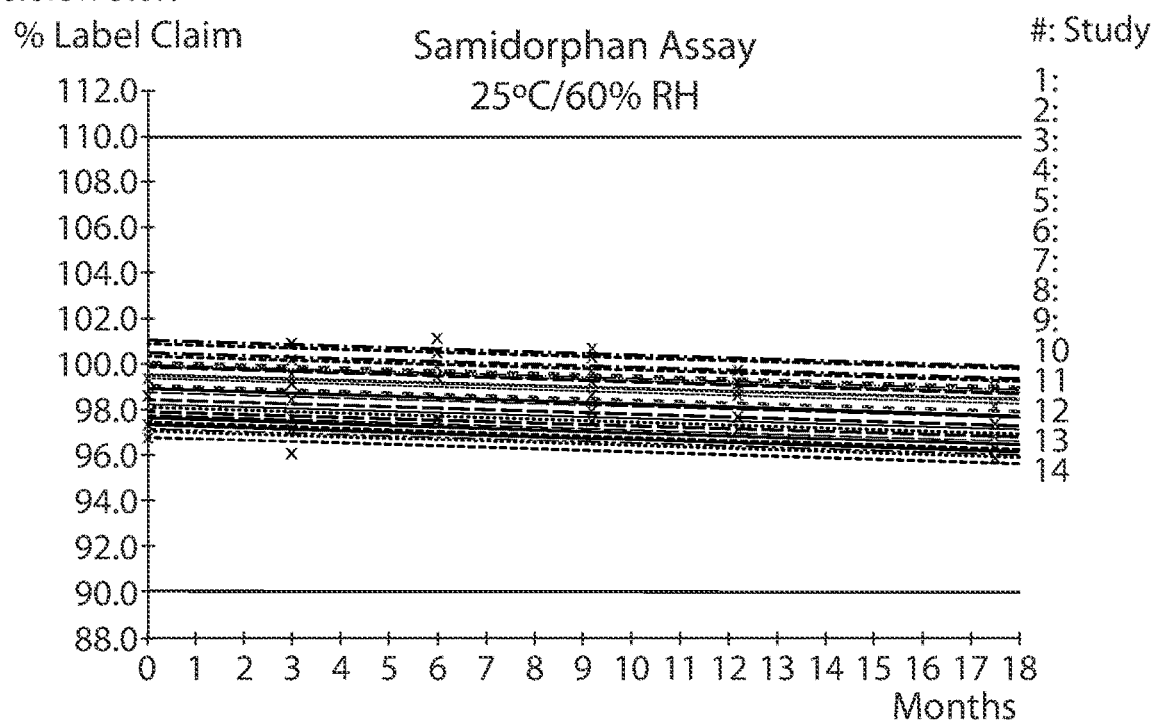
FIG. 5 depicts exemplary shelf life studies of samidorphan in disclosed tablets as represented by regression analyses.
Figure 6:
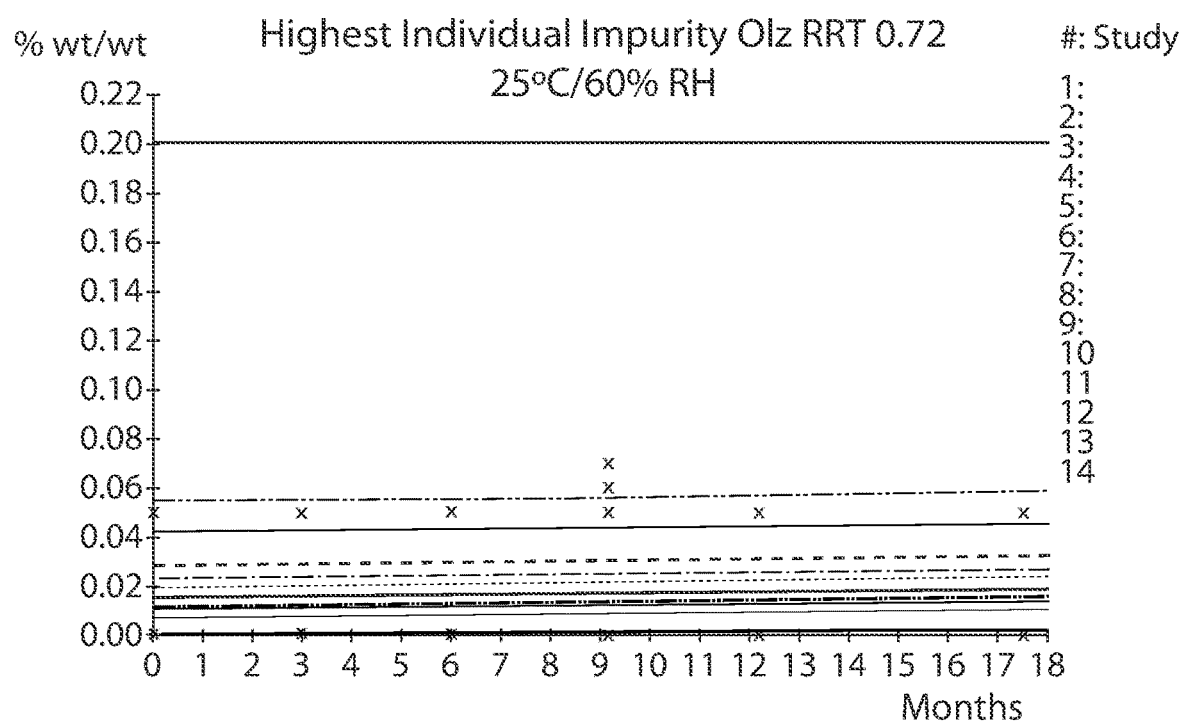
FIG. 6 depicts exemplary shelf life studies of highest-related impurity amounts in disclosed tablets as represented by regression analyses.
Figure 7:
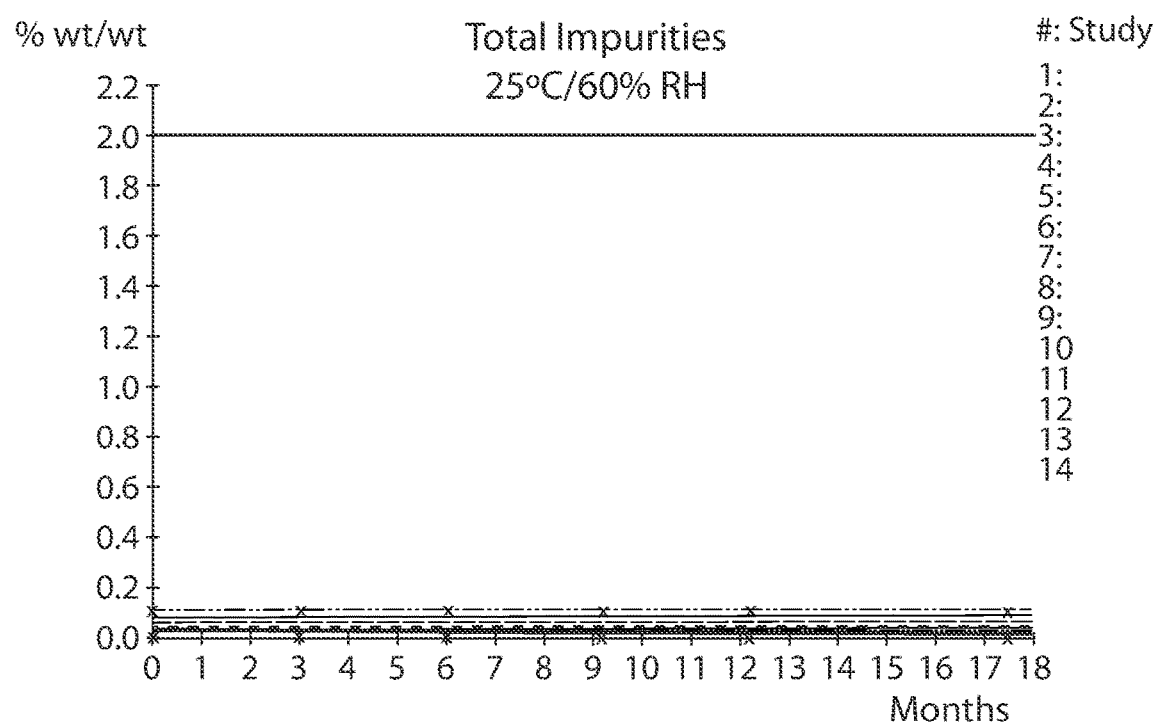
FIG. 7 depicts exemplary shelf life studies of total-related impurity amounts in disclosed tablets as represented by regression analyses.
Figure 8:
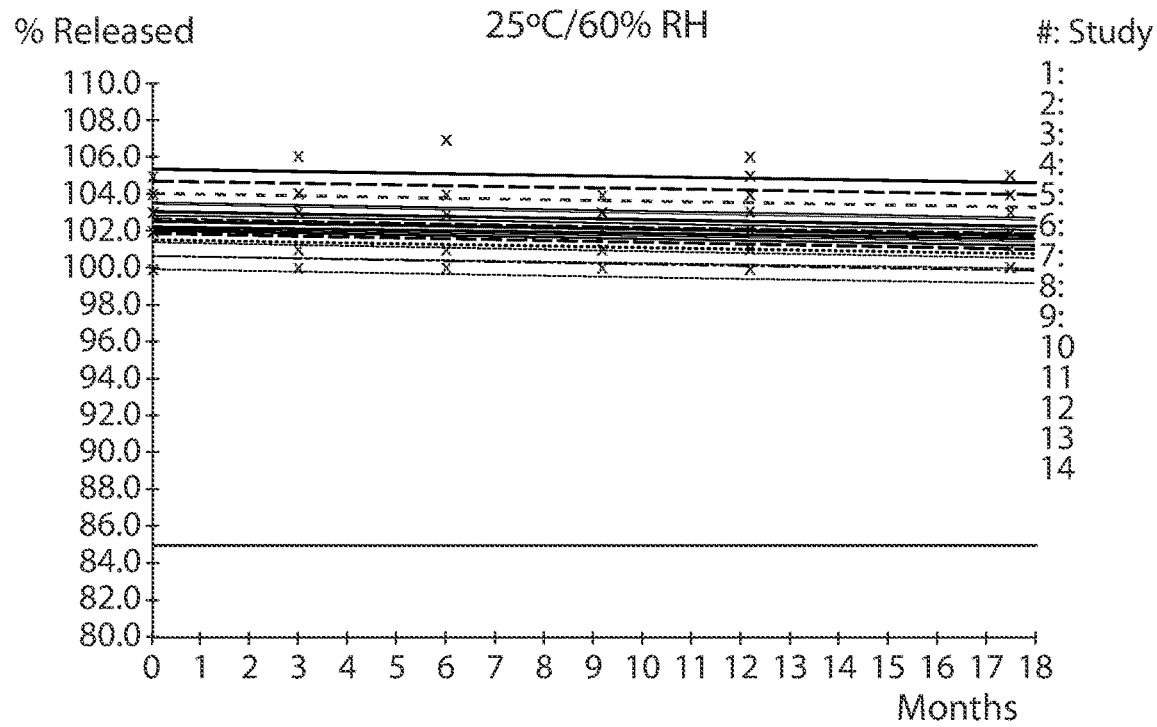
FIG. 8 depicts exemplary shelf life studies of olanzapine dissolution at 30 minutes as represented by regression analyses.
Figure 9:
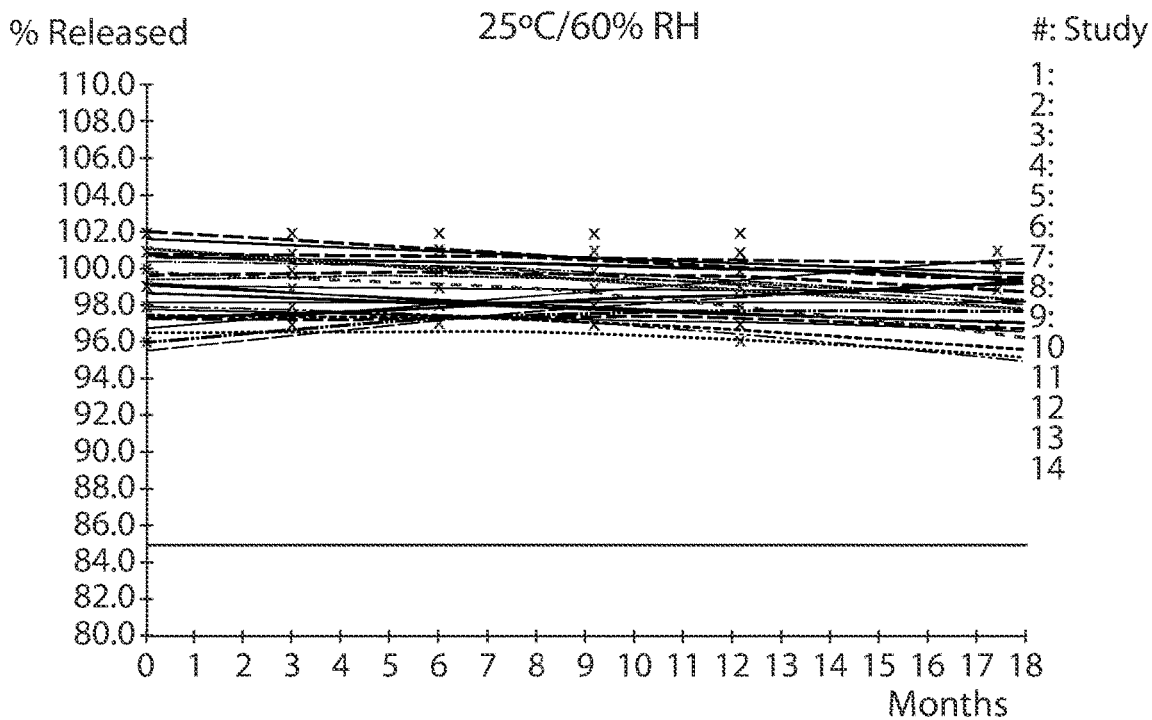
FIG. 9 depicts exemplary shelf life studies of samidorphan dissolution at 30 minutes as represented by regression analyses.
Figure 10:
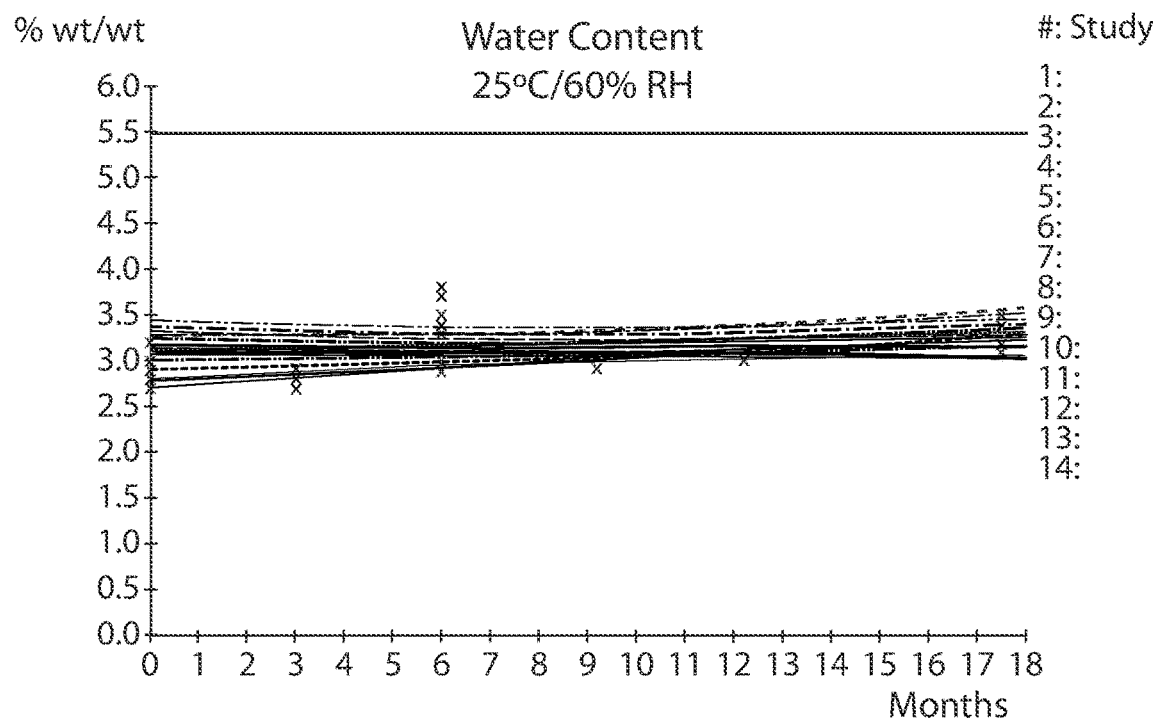
FIG. 10 depicts exemplary shelf life studies of water content in disclosed tablets as represented by regression analyses.

| Test Attribute | Model | Regression Analysis | Expiry | |
|---|---|---|---|---|
| Assay | 2 | FIG. 4 | OLZ | 113 months |
| % | 2 | FIG. 4 | SAM | 84 months |
| Highest Related Impurity (% wt/wt) | 2 | FIG. 5 | | 211 months |
| Total Related Impurities (% wt/wt) | 2 | FIG. 6 | | 1331 months |
| Dissolution, % release at 30 minutes | 2 | FIG. 7 | OLZ | 211 months |
| | 4 | FIG. 8 | SAM | 54 months |
| Water Content (% wt/wt) | 4 | FIG. 10 | | 51 months |

For batches in Table 17, regression analyses of test attributes (Assay for %, Highest Related Impurity, Total Related Impurities, Dissolution, % release at 30 minutes, and Water Content) are provided in FIGS. 4, 5, 6, 7, 8, 9, and 10, respectively.

The supportive stability batches were packaged identically to the primary stability batches. The results of the statistical analysis demonstrate that the stability data from the supportive batches are comparable to the stability data from the primary stability batches.

In-Use Stability Study.

An in-use stability study was conducted to unit dose repackaging in a hospital setting. The stability study is currently ongoing utilizing one 5 mg/10 mg OLZ/SAM batch and one 20 mg/10 mg OLZ/SAM batch stored at the intended storage condition of 25° C.±2° C./60%±5% RH. To reproduce representative hospital handling, the samples were repackaged into amber unit-dose blisters. Exemplary results for each batch up to 6 months are shown in Table 18 (5 mg/10 mg OLZ/SAM) and Table 19 (20 mg/10 mg OLZ/SAM).

TABLE 18

5 mg/10 mg OLZ/SAM Results for In-Use Stability Study at 25° C./60% RH.

| Test | Initial | | 3 months | | 6 months | |
|---|---|---|---|---|---|---|
| Description | Conforms | | Conforms | | Conforms | |
| Assay (%) | OLZ | SAM | OLZ | SAM | OLZ | SAM |
| | 101.0% | 99.7% | 99.8% | 100.0% | 99.5% | 99.3% |
| Total Related Impurities (% wt/wt) | 0.1% | | 0.1% | | 0.2% | |
| Dissolution (% Release at 30 min) | OLZ | SAM | OLZ | SAM | OLZ | SAM |
| | 103% | 101% | 102% | 100% | 101% | 100% |
| Water Content (% wt/wt) | 4.7% | | 5.1% | | 5.4% | |

TABLE 19

20 mg/10 mg OLZ/SAM Results for In-Use Stability Study at 25° C./60% RH.

| Test | Initial | | 3 months | | 6 months | |
|---|---|---|---|---|---|---|
| Description | Conforms | | Conforms | | Conforms | |
| Assay (%) | OLZ | SAM | OLZ | SAM | OLZ | SAM |
| | 101.1% | 101.7% | 100.7% | 101.5% | 100.3% | 101.2% |
| Total Related Impurities (% wt/wt) | 0.0% | | 0.1% | | 0.1% | |
| Dissolution (% Release at 30 min) | OLZ | SAM | OLZ | SAM | OLZ | SAM |
| | 103% | 102% | 103% | 104% | 101% | 102% |
| Water Content (% wt/wt) | 4.7% | | 5.1% | | 5.2% | |

Example 7: Clinical Study 1

Clinical Study 1 was a Phase 1, multicenter, open-label, randomized study designed to determine the steady-state pharmacokinetic profile of olanzapine and samidorphan and to evaluate the safety and tolerability of olanzapine and samidorphan bilayer tablets in adult subjects with schizophrenia following 14 consecutive days of oral administration.

Prior to commencement, subjects taking antipsychotic medication at study entry were tapered off their medication and titrated to olanzapine (15 mg/day) during a 1 week lead-in period. Following olanzapine lead-in, 42 subjects were randomly assigned (1:1) to receive an oral bilayer tablet of Formulation C (10/10, i.e. 10 mg olanzapine and 10 mg samidorphan as described in Table 4 herein) once daily or Formulation B (20/10, i.e. 20 mg olanzapine and 10 mg samidorphan as described in Table 6 herein) once daily for 14 days (Days 1 to 14).

Blood samples for PK assessments were collected before dosing (predose) and at 0.5, 1, 2, 3, 4, 5, 6, 7, 8, 12, 16, and 24 h after dosing of Formulations B (20/10) and C (10/10) described above on Day 1 and Day 14. Additional trough samples were collected predose on Days 3 to 13 of the study.

Pharmacokinetic Results

Figure 11:
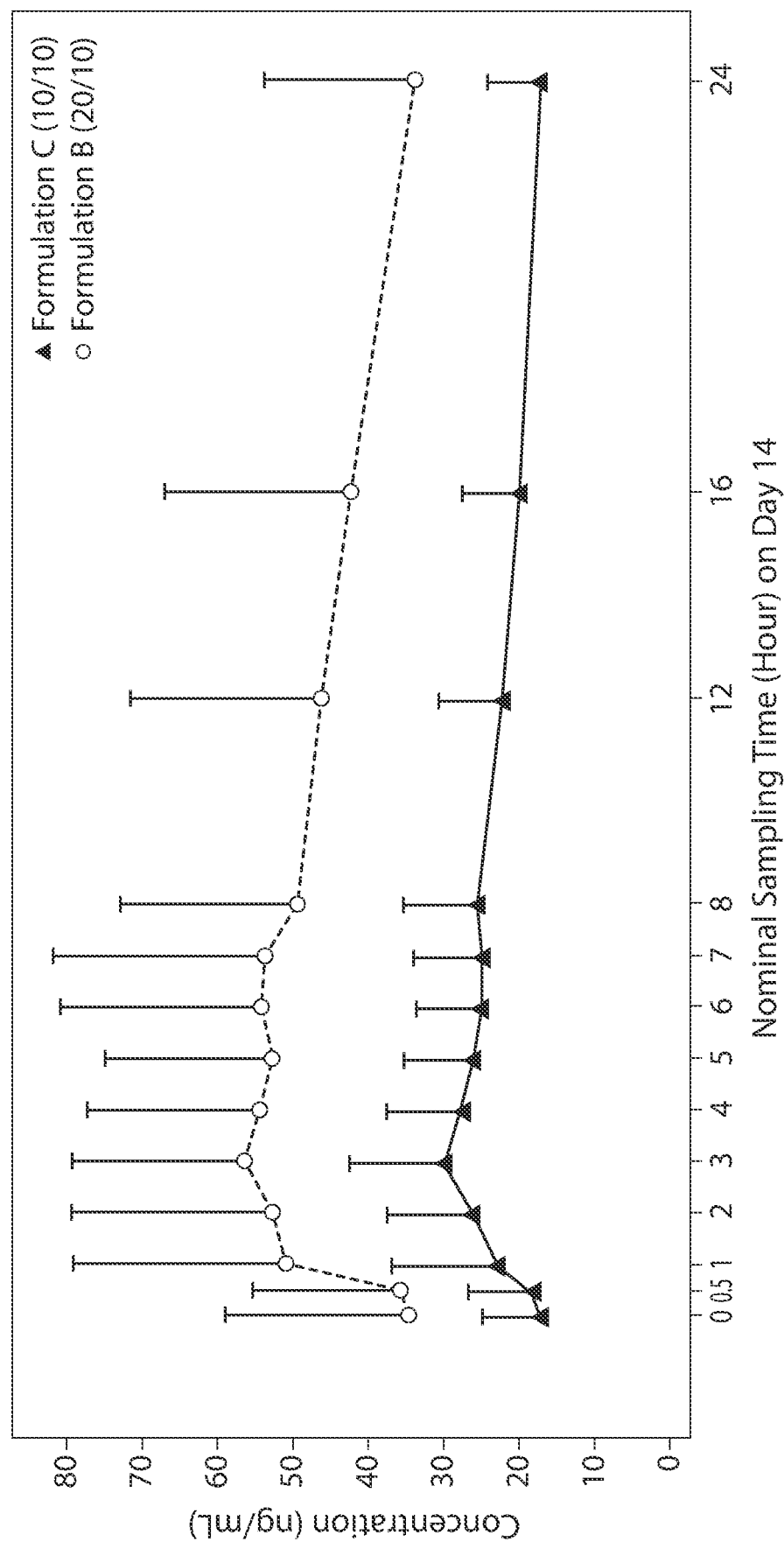
FIG. 11 depicts mean (and standard deviation) plasma concentrations of olanzapine as observed on Day 14 of the pharmacokinetic population study (titled Clinical Study 1) described in Example 7 herein.
Figure 12:
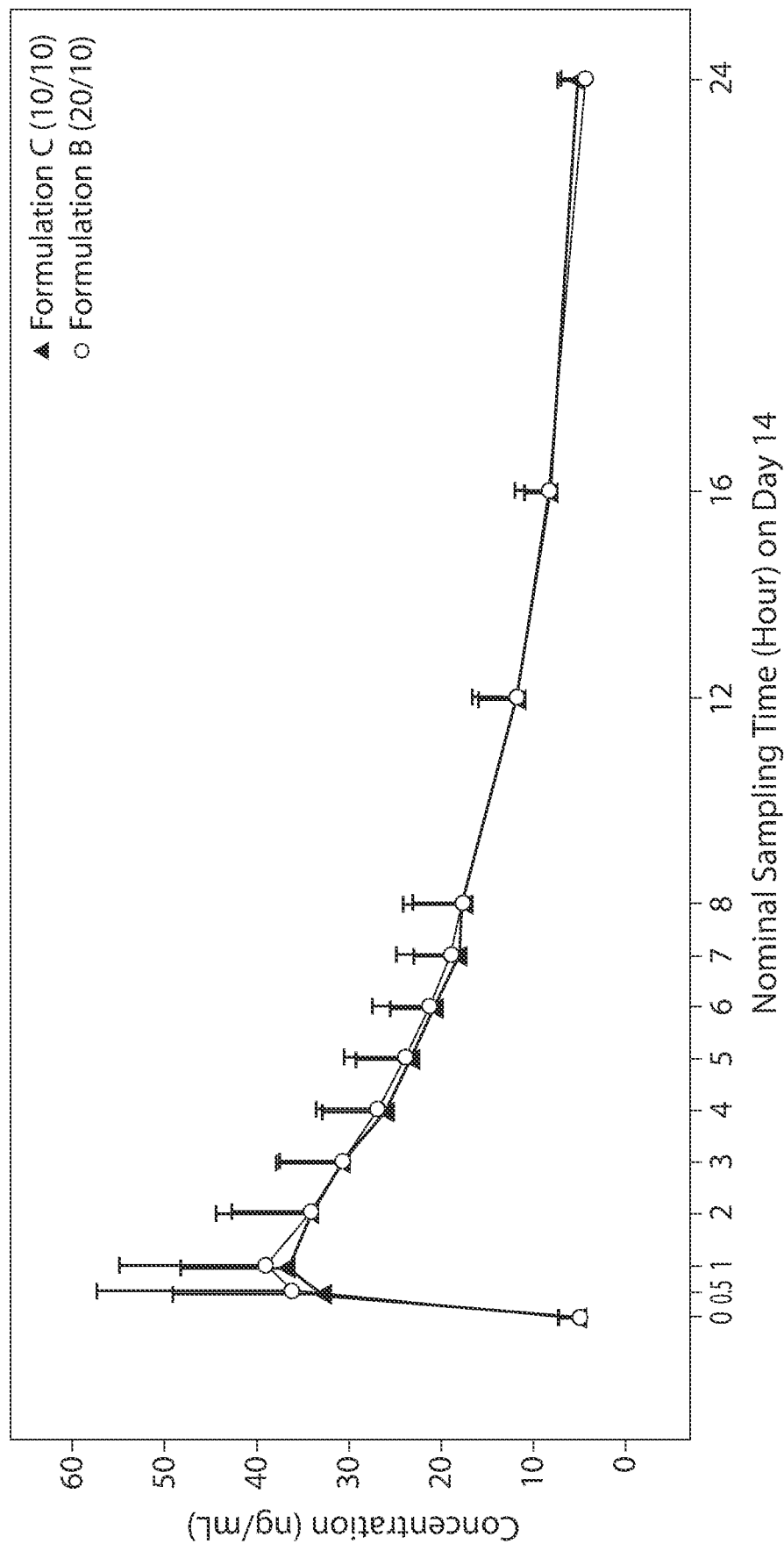
FIG. 12 depicts mean (and standard deviation) plasma concentrations of samidorphan as observed on Day 14 of the pharmacokinetic population study (titled Clinical Study 1) described in Example 7 herein.

Mean steady state (Day 14) olanzapine and samidorphan plasma concentration-time profiles for both treatment groups are presented in FIG. 11 and FIG. 12 respectively. The key steady state pharmacokinetic parameters are summarized in Table 20. Steady state (Day 14) olanzapine exposure (maximum plasma concentration ($C_{max}$) and area under the concentration-time curve from time 0 to 24 hours postdose ($AUC_{0-24}$) increased dose proportionally with the increase in olanzapine dose from 10 mg (Formulation C (10/10)) to 20 mg (Formulation B (20/10)).

After oral administration of Formulation B (20/10) and C (10/10), samidorphan was rapidly absorbed with mean $C_{max}$ reached within 1 hour post dose. The mean concentration-time profiles of samidorphan were almost superimposable for both treatment groups (FIG. 12).

TABLE 20

Pharmacokinetic parameters for olanzapine and samidorphan after once-daily oral administration of Formulation C (10/10) or Formulation B (20/10) for 14 days; Day 14 data.

| Treatment; N | PK Parameter[a] | olanzapine | samidorphan |
|---|---|---|---|
| Formulation C 10/10 QD N = 21 | $C_{max}$ (ng/mL) | 32.1 (12.4) | 43.1 (11.4) |
| | $t_{max}$ (hr) | 3 (1.00, 8.00) | 1 (0.48, 3.00) |
| | $AUC_{0-24}$ (ng · hr/mL) | 533 (196) | 360 (99.5) |
| Formulation B 20/10 QD N = 21 | $C_{max}$ (ng/mL) | 64.6 (28.9) | 46.0 (15.1) |
| | $t_{max}$ (hr) | 3 (0.98, 8.20) | 1 (0.48, 4.00) |
| | $AUC_{0-24}$ (ng · hr/mL) | 1086 (556) | 364 (112) |

[a]Data are presented as Arithmatic Mean (SD) except for $t_{max}$, which is summarized as median (minimum, maximum).

Abbreviations:
$AUC_{0-24}$ = area under the concentration-time curve from time 0 to 24 hr;
$C_{max}$ = maximum observed concentration;
QD = once daily;
SD = standard deviation
$t_{max}$ = time to maximum observed concentration.

The pharmacokinetic profile of olanzapine, as a component of Formulation B and Formulation C, was found to be comparable with previously published data for olanzapine administered alone (see e.g. Callaghan J T, Bergstrom R F, Ptak L R, Beasley C M. Olanzapine: pharmacokinetic and pharmacodynamic profile. Clin Pharmacokinet. 1999; 37:177-193). The pharmacokinetic profile of samidorphan was not affected by different dose levels of olanzapine in the combination. The data from this study indicated that combining olanzapine with samidorphan in a bilayer tablet does not affect the pharmacokinetic profile of either drug.

Example 8: Clinical Study 2

This study was a Phase 1, single-center, open-label, randomized, balanced, crossover design study in a total of 48 healthy subjects to determine the relative bioavailability of olanzapine after single dose oral administration of the bilayer tablet of Formulation C, olanzapine/placebo bilayer tablet (referred to herein as ALKS olanzapine), and a branded olanzapine tablet marketed under the brand name Zyprexa® (registered trademark of Eli Lilly and Company), referred to herein as Branded olanzapine. The study was designed and powered to evaluate the bioequivalence of olanzapine between the three olanzapine-containing tablet formulations.

The study consisted of three periods, each including a 4-day inpatient stay and a 5-day outpatient follow-up. A single dose of study drug was administered on Day 1 of each period separated by a 14-day washout between doses. Subjects meeting the eligibility criteria receives a single dose of Formulation C (10/10) (10 mg olanzapine and 10 mg samidorphan) as described in Example 3, table 5 above, ALKS olanzapine which was a 10 mg olanzapine/placebo bilayer tablet, and Branded olanzapine (10 mg olanzapine) on Day 1 of Period 1.

Blood samples for PK assessments were collected within 15 minutes before dosing (predose) and 0.5, 1, 2, 3, 4, 5, 6, 7, 8, 12, 16, 24, 32, 48, 72, 96, 120, and 168 hours postdose.

Pharmacokinetic Results

Figure 13:
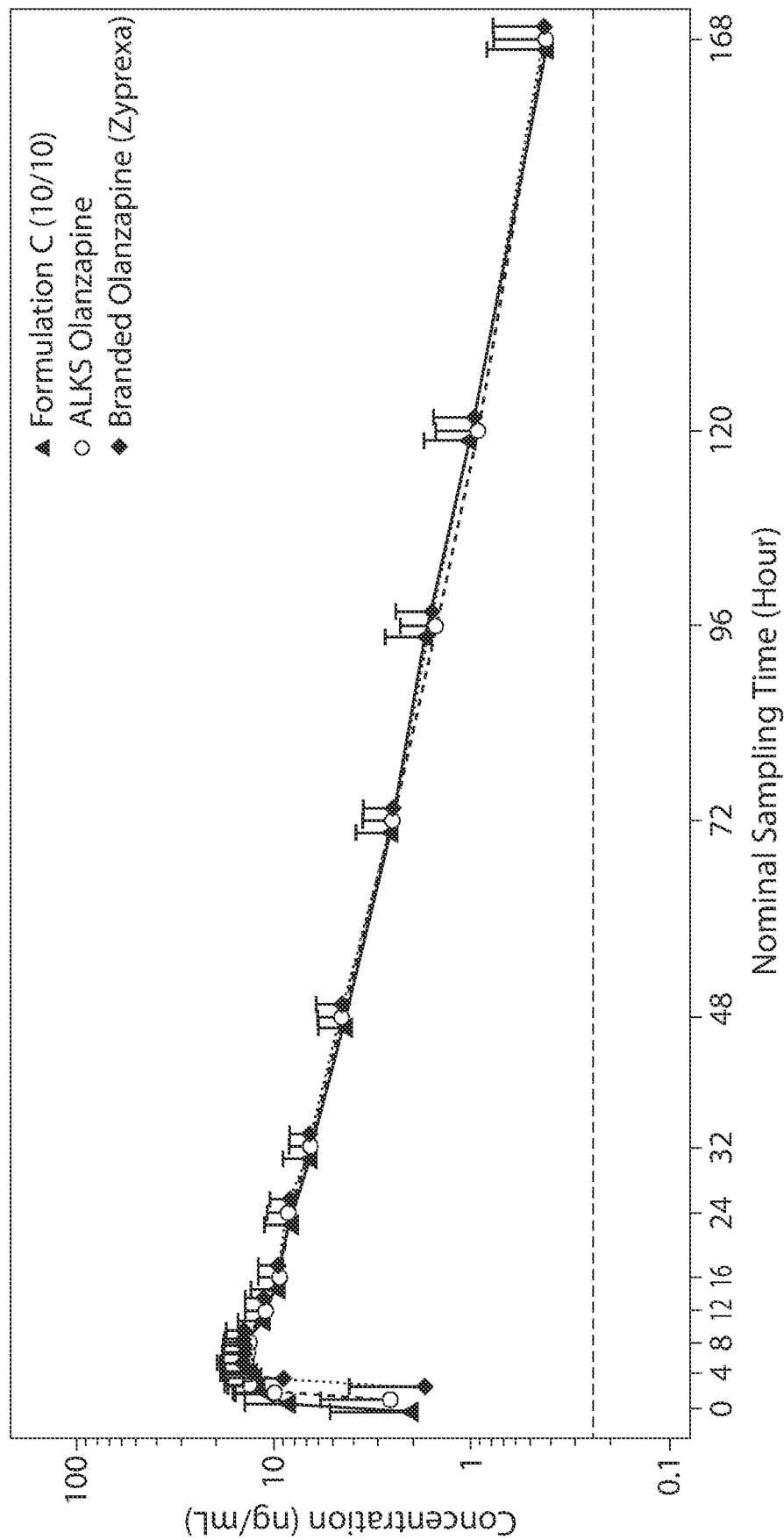
FIG. 13 depicts mean (and standard deviation) plasma concentrations of olanzapine as observed in the pharmacokinetic population study (titled Clinical Study 2) described in Example 8 herein.

The pharmacokinetic profiles of olanzapine after a single dose administration of Formulation C (10/10), ALKS Olanzapine (10 mg), and Branded olanzapine (10 mg) were superimposable (FIG. 13). Pharmacokinetic parameters, including $C_{max}$, $t_{max}$, $AUC_{last}$, and $AUC_{\infty}$, are summarized in Table 21. The olanzapine component in Formulation C (10/10) and ALKS Olanzapine bilayer tablets was demonstrated to be bioequivalent to the Branded olanzapine.

TABLE 21

Pharmacokinetic parameters for olanzapine after single-dose administration of Formulation C (10 mg olanzapine/10 mg samidorphan), ALKS olanzapine (10 mg olanzapine/placebo bilayer tablet) and Branded olanzapine (10 mg olanzapine)

| Parameter Statistics | Formulation C (10 mg samidorphan/ 10 mg olanzapine) | ALKS olanzapine (10 mg olanzapine/ placebo) | Branded olanzapine (10 mg)) |
|---|---|---|---|
| n | 46 | 45 | 48 |
| $C_{max}$, ng/mL Mean (SD) | 16.6 (4.5) | 16.7 (4.2) | 16.6 (3.8) |
| tmax, h Median (min-max) | 7.0 (2.0-16.0) | 5.0 (2.0-12.0) | 5.0 (2.0-12.0) |
| $AUC_{0-t}$, ng h/mL Mean (SD) | 610.6 (215.7) | 599.1 (187.8) | 594.3 (190.8) |
| $AUC_{0-\infty}$, ng h/mL Mean (SD) | 652.0 (226.5) | 629.2 (205.0) | 632.6 (197.2) |

Abbreviations:
$C_{max}$ = maximum plasma concentration
$t_{max}$ = time to reach maximum plasma concentration
$AUC_\infty$ = area under the plasma concentration-time curve from time zero extrapolated to infinity
$AUC_{0-t}$ = area under the plasma concentration-time curve from time zero until the last measurable concentration time point
SD = standard deviation
n = number of subjects whose parameter values are in the summary statistics Samidorphan Administered as a Component in Formulation C compared with Samidorphan Administered Alone Key pharmacokinetic parameters of samidorphan after a single dose administration of Formulation C (10 mg olanzapine/10 mg samidorphan) are depicted below in Table 22. For comparison, these parameter values are shown alongside data obtained from a separate clinical study conducted by the Applicant, when administered as samidorphan alone in tablet form.

TABLE 22

Pharmacokinetic Parameters for Samidorphan after single-dose administration of Formulation C (10 mg olanzapine/10 mg samidorphan) as compared to samidorphan alone in selected studies

| Treatment (Dose) | Olanzapine/samidorphan (10 mg/10 mg) | Samidorphan alone (10 mg) |
|---|---|---|
| Study Type | Clinical Study 2 | Human Abuse Potential Study |
| Study (N) | 45 | 56 |
| $C_{max}$ (ng/mL) Mean (SD) | 27.8 (9.9) | 28.2 (6.2) |
| $t_{max}$, (h) Median (min-max) | 2.0 (0.5-6.0) | 1.5 (0.5-4.0) |
| $AUC_{(0-t)}$, (h · ng/mL) Mean (SD) | 240.0 (57.6) | 224.9 (55.9) |
| $AUC_{(0-\infty)}$, (h · ng/mL) Mean (SD) | 245.6 (56.9) | 230.1 (56.7) |

Abbreviations:
$C_{max}$ = maximum plasma concentration;
$t_{max}$ = time to reach maximum plasma concentration
$AUC_\infty$ = Area under plasma concentration time curve extrapolated to infinity;
$AUC_{(0-t)}$, area under the plasma concentration-time curve from zero to the last quantifiable concentration
N = number of subjects per treatment group;
SD = standard deviation The above studies clearly demonstrate that when Formulation C (10/10) was administered in vivo, the pharmacokinetic profile of the samidorphan and olanzapine were not significantly affected by presenting both actives together in a bilayer configuration.

EQUIVALENTS

While specific embodiments have been discussed, the above specification is illustrative and not restrictive. Many variations of the present disclosure will become apparent to those skilled in the art upon review of this specification. The full scope of the present disclosure should be determined by reference to the claims, along with their full scope of equivalents, and the specification, along with such variations.

What is claimed is:

1. A method of treating schizophrenia or bipolar I disorder in a patient in need thereof, the method comprising orally administering to the patient, once daily, a pharmaceutically acceptable coated immediate release bilayer tablet for orally delivering a fixed dose of olanzapine and 10 mg of samidorphan, wherein the bilayer tablet comprises:
  a first tablet layer comprising:
    10 mg samidorphan or a pharmaceutically acceptable salt of samidorphan in an amount to deliver 10 mg samidorphan;
    about 35-43 wt % microcrystalline cellulose, based on the weight of the first tablet layer;
    about 37-43 wt % lactose or a hydrate thereof, based on the weight of the first tablet layer; and
    about 1.5 to about 2 wt % magnesium stearate;
  a second tablet layer comprising:
    a dose of olanzapine selected from the group consisting of 5 mg, 10 mg, 15 mg and 20 mg of the olanzapine;
    about 38-42 wt % microcrystalline cellulose, based on the weight of the second tablet layer;
    about 46-49 wt % lactose or a hydrate thereof, based on the weight of the second tablet layer; and
    about 1.0 wt % magnesium stearate;
  and
  a film coating over the first and second tablet layer, wherein the tablet releases at least 97% of olanzapine and at least 97% of the samidorphan after 30 minutes when the tablet is tested in 500 mL USP acetate buffer at pH 1.0 using a USP Apparatus II (Paddle Method) at 37 with a paddle speed of 75 rpm and using a three-prong sinker.

2. The method of claim 1, wherein the tablet releases at least 97% of olanzapine and at least 97% of the samidorphan after 30 minutes when the tablet is tested in 500 mL USP acetate buffer at pH 4.5 using a USP Apparatus II (Paddle Method) at 37° C., with a paddle speed of 75 rpm and using a three-prong sinker.

3. The method of claim 1, wherein the pharmaceutically acceptable salt of samidorphan in amount to deliver 10 mg samidorphan is 13.6 mg samidorphan L-malate.

4. The method of claim 1, wherein less than 0.5 wt % impurities from olanzapine degradation are detected, using HPLC, after the tablet is stored for 6 month in a closed container containing 250 g silica gel desiccant at 25° C. and 60% relative humidity.

5. The method of claim 1, wherein the first tablet layer further comprises about 2.0 wt % crospovidone and the second tablet layer further comprises about 1.0 wt % crospovidone.

6. The method of claim 1, wherein the dose of olanzapine is 5 mg.

7. The method of claim 1, wherein the dose of olanzapine is 10 mg.

8. The method of claim 1, wherein the dose of olanzapine is 15 mg.

9. The method of claim 1, wherein the dose of olanzapine is 20 mg.

10. A method of treating schizophrenia or bipolar I disorder in a patient in need thereof, the method comprising orally administering to the patient, once daily, a pharmaceutically acceptable coated immediate release bilayer tablet for orally delivering a fixed dose of olanzapine and 10 mg of samidorphan, wherein the bilayer tablet comprises:
a first tablet layer comprising:
13.6 mg samidorphan L-malate; about 40 wt % microcrystalline cellulose, based on the weight of the first tablet layer; about 42 wt % lactose monohydrate, based on the weight of the first tablet layer; and about 1.75 wt % magnesium stearate; and
a second tablet layer comprising:
a dose of olanzapine selected from the group consisting of 5 mg, 10 mg, 15 mg and 20 mg of the olanzapine; about 40 wt % microcrystalline cellulose, based on the weight of the second tablet layer; about 47 wt % lactose or a hydrate thereof, based on the weight of the second tablet layer; and about 1.0 wt % magnesium stearate; and a film coating over the first and second tablet layer,
wherein the tablet releases at least 97% of olanzapine and at least 97% of the samidorphan after 30 minutes when the tablet is tested in 500 mL USP acetate buffer at pH 1.0 using a USP Apparatus II (Paddle Method) at 37 with a paddle speed of 75 rpm and using a three-prong sinker.

11. The method of claim 10, wherein the samidorphan L-malate has a particle size distribution (D10) of about 10 μm to about 80 μm, a particle size distribution (D50) of about 40 μm to about 200 μm, and a particle size distribution (D90) of about 100 μm to about 300 μm.

12. A method of treating schizophrenia or bipolar I disorder in a patient in need thereof, the method comprising orally administering to the patient, once daily, a pharmaceutically acceptable coated immediate release bilayer tablet for orally delivering olanzapine and 10 mg of samidorphan as a fixed dose, comprising:
a first tablet layer comprising:
10 mg samidorphan or a pharmaceutically acceptable salt of samidorphan in an amount to deliver 10 mg samidorphan;
about 35-43 wt % microcrystalline cellulose, based on the weight of the first tablet layer; and
about 37-43 wt % lactose or a hydrate thereof, based on the weight of the first tablet layer;
a second tablet layer comprising:
a dose of olanzapine selected from the group consisting of 5 mg, 10 mg, 15 mg and 20 mg of the olanzapine;
about 38-42 wt % microcrystalline cellulose, based on the weight of the second tablet layer;
about 46-49 wt % lactose or a hydrate thereof, based on the weight of the second tablet layer;
and
a film coating over the first and second tablet layer;
wherein the bi-layer tablet releases at least 85% of olazanpine and at least 85% of the samidorphan after 15 minutes when the bi-layer tablet is tested in 500 mL USP acetate buffer at pH 4.5 using a USP Apparatus II (Paddle Method) at 37° C., with a paddle speed of 75 rpm and using a three-prong sinker.

13. A method of treating schizophrenia or bipolar I disorder in a patient in need thereof, the method comprising orally administering to the patient, once daily, a pharmaceutically acceptable coated immediate release bilayer tablet for orally delivering, as a fixed dose, olanzapine and 10 mg of samidorphan wherein the bilayer tablet, comprises:
a first tablet layer comprising:
10 mg samidorphan or a pharmaceutically acceptable salt of samidorphan in an amount to deliver 10 mg samidorphan; about 30-45 wt % microcrystalline cellulose, based on the weight of the first tablet layer; about 35-50 wt % lactose or a hydrate thereof, based on the weight of the first tablet layer;
a second tablet layer comprising:
a dose of olanzapine selected from the group consisting of 2.5 mg, 5 mg, 10 mg, 15 mg and 20 mg of the olanzapine; about 35-45 wt % microcrystalline cellulose, based on the weight of the second tablet layer; about 45-55 wt % lactose or a hydrate thereof, based on the weight of the second tablet layer; and a film coating over the first and second tablet layer,
wherein the tablet releases at least 97% of olanzapine and at least 97% of the samidorphan after 30 minutes when the tablet is tested in 500 mL USP acetate buffer at pH 1.0 using a USP Apparatus II (Paddle Method) at 37 with a paddle speed of 75 rpm and using a three-prong sinker.

* * * * *